United States Patent
Ting et al.

(10) Patent No.: US 9,971,876 B2
(45) Date of Patent: *May 15, 2018

(54) METHOD, SYSTEM AND ELECTRONIC DEVICE FOR DIET MANAGEMENT

(71) Applicant: Industrial Technology Research Institute, Hsinchu (TW)

(72) Inventors: Chuan-Wei Ting, Kaohsiung (TW); Ching-Yao Wang, Tainan (TW); Ju-Chin Chen, Hualien County (TW)

(73) Assignee: Industrial Technology Research Institute, Hsinchu (TW)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/232,829

(22) Filed: Aug. 10, 2016

(65) Prior Publication Data

US 2016/0350515 A1  Dec. 1, 2016

Related U.S. Application Data

(62) Division of application No. 13/854,970, filed on Apr. 2, 2013, now Pat. No. 9,449,029.

(30) Foreign Application Priority Data

Dec. 14, 2012  (TW) .............................. 101147599 A

(51) Int. Cl.
G06T 7/11 (2017.01)
G06F 19/00 (2018.01)
G06F 17/30 (2006.01)
G09B 19/00 (2006.01)
G06K 9/00 (2006.01)

(52) U.S. Cl.
CPC .... *G06F 19/3475* (2013.01); *G06F 17/30256* (2013.01); *G06F 17/30271* (2013.01); *G06F 17/30598* (2013.01); *G06F 19/321* (2013.01); *G06K 9/00* (2013.01); *G09B 19/0092* (2013.01)

(58) Field of Classification Search
None
See application file for complete search history.

(56) References Cited

U.S. PATENT DOCUMENTS 8,165,414 B1 * 4/2012 Yagnik ................ G06F 17/3002
                                                    382/236
2002/0027164 A1 * 3/2002 Mault .................. A61B 5/1118
                                                    235/462.46

(Continued)

*Primary Examiner* — Wilson Lee
(74) *Attorney, Agent, or Firm* — JCIPRNET

(57) ABSTRACT

An electronic device, a system and a method for diet management based on image analysis are provided. The system includes a computer and a database. The computer comprises a processor for performing the following operations: capturing at least one diet image via an image capture device; pre-processing the at least one diet image so as to obtain at least one diet region from the at least one diet image and obtain at least one detailed food segment from the diet region; extracting at least one diet image feature from the at least one detailed food segment; determining a diet type of the at least one detailed food segment based on the at least one diet image feature; and providing a personal diet characteristic analysis based on the diet type and an area of the at least one detailed food segment.

18 Claims, 19 Drawing Sheets

(56) References Cited

U.S. PATENT DOCUMENTS

| | | | |
|---|---|---|---|
| 2008/0144880 A1* | 6/2008 | DeLuca | G06T 7/20 |
| | | | 382/100 |
| 2009/0323131 A1* | 12/2009 | Toyoda | G06T 3/608 |
| | | | 358/448 |
| 2010/0111383 A1* | 5/2010 | Boushey | G06K 9/00 |
| | | | 382/128 |
| 2010/0173269 A1* | 7/2010 | Puri | G09B 19/0092 |
| | | | 434/127 |
| 2012/0170801 A1* | 7/2012 | De Oliveira | G06K 9/6256 |
| | | | 382/103 |
| 2012/0179665 A1* | 7/2012 | Baarman | G06F 19/3475 |
| | | | 707/709 |
| 2014/0343431 A1* | 11/2014 | Vajinepalli | A61B 8/06 |
| | | | 600/454 |

\* cited by examiner

METHOD, SYSTEM AND ELECTRONIC DEVICE FOR DIET MANAGEMENT

CROSS-REFERENCE TO RELATED APPLICATION

This application is a divisional application of U.S. application Ser. No. 13/854,970, filed on Apr. 2, 2013, now allowed, which claims the priority benefit of Taiwan application serial no. 101147599, filed on Dec. 14, 2012. The entirety of each of the above-mentioned patent applications is hereby incorporated by reference herein and made a part of this specification.

TECHNICAL FIELD

The disclosure relates to a method, a system and an electronic device for diet management.

BACKGROUND

In recent years, due to the human diet containing high-calorie, high-fat, and high-glycemic index food as well as insufficient exercise, more and more people are getting gastrointestinal diseases and cardiovascular diseases, and the age of getting such diseases is getting younger. In tennis of the expenditure in medical care, the gastrointestinal diseases (including colorectal cancer and rectal cancer), the cardiovascular diseases (including heart attacks, stroke, and hypertension) and the related expenses have caused too much pressure on people's health and medical resources. In order to prevent from gastrointestinal diseases and cardiovascular diseases, many nutritionists have been promoting the importance of healthy diet and indicating that improperiate diet is a main reason of getting each of the adult chronic diseases and accelerating aging.

According to the World Health Organization (WHO), 75% of the modern people are under the sub-healthy state, 25% of the people are having diseases, and only 5% of the people are truly healthy. Among the three factors (genetics, living environment, and diet nutrition) that affect the health, only the diet nutrition may be personally controlled. A conventional diet management method provides information for disease or nutrition analysis by filling up personal data sheets. However, since the record-filling steps are too tedious so that a user's willingness to use is inevitably reduced.

Hence, assisting the user to manage diet intakes and diet habits by using information technology is one of the ultimate goals in medical and information fields. Additionally, assisting the user to collect personal diet activity as well as analyzing the characteristics of the provided diet information by using information technology is one of the recent research topics.

SUMMARY

The present disclosure is directed to a method, a system and an electronic device for diet management determines a diet type based on a diet image and providing a personal diet characteristic analysis.

A computer-implemented method for diet management, adapted to a diet management system comprising a computer and a memory device used as a database, is provided according to an embodiment of the present disclosure. The computer comprises a processor and a plurality of program instructions, wherein the plurality of program instructions are loaded into the processor to perform the computer-implemented method. The computer-implemented method includes the followings. Capture at least one diet image via an image capture device. Pre-process the at least one diet image so as to obtain at least one diet region from the at least one diet image and obtain at least one detailed food segment from the diet region. Extracts at least one diet image feature from the at least one detailed food segment. Determines a diet type of the at least one detailed food segment based on the at least one diet image feature. Provides a personal diet characteristic analysis based on the diet type and an area of the at least one detailed food segment.

A system for diet management, comprising a computer and a memory device used as a database, is provided according to an embodiment of the present disclosure. The computer comprises a processor and a plurality of program instructions, wherein the plurality of program instructions are loaded into the processor to perform the following operations: capturing at least one diet image via an image capture device; pre-processing the at least one diet image so as to obtain at least one diet region from the at least one diet image and obtain at least one detailed food segment from the diet region; extracting at least one diet image feature from the at least one detailed food segment; determining a diet type of the at least one detailed food segment based on the at least one diet image feature; and providing a personal diet characteristic analysis based on the diet type and an area of the at least one detailed food segment.

An electronic device, comprising a database and a processing circuit, is provided according to an embodiment of the present disclosure. The processing circuit is electrically coupled to the database. The processing circuit captures at least one diet image via an image capture device. The processing circuit pre-processes the at least one diet image so as to obtain at least one diet region from the at least one diet image and obtain at least one detailed food segment from the diet region. The processing circuit extracts at least one diet image feature from the at least one detailed food segment. The processing circuit determines a diet type of the at least one detailed food segment based on the at least one diet image feature, and provides a personal diet characteristic analysis based on the diet type and an area of the at least one detailed food segment.

To sum up, the method, the system and the electronic device for diet management provided according to some other embodiments of the present disclosure determines a diet type based on a diet image and providing a personal diet characteristic analysis.

Several exemplary embodiments accompanied with figures are described in detail below to further describe the disclosure in details.

DETAILED DESCRIPTION OF DISCLOSED EMBODIMENTS

Figure 1:
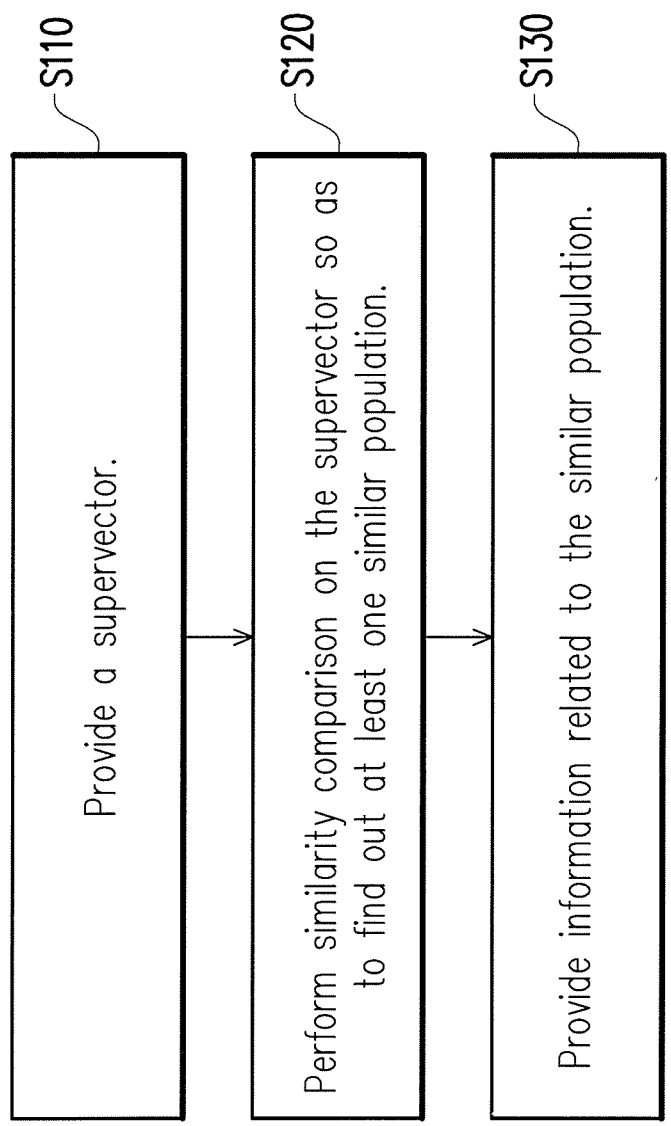
FIG. 1 is a flowchart of a method for diet management according to an embodiment of the present disclosure.

In the following description and claims, the term "couple" may be used to indicate any direct or indirect connection method. For example, if it is described that a first device is coupled to a second device, it should be interpreted that the first device may be connected to the second device directly or the first device may be connected to the second device indirectly via other devices or other connection methods. Moreover, whenever possible in the following description and figures, in which the same reference numerals refer to the same or comparable elements/components/steps. In different embodiments, the same reference numerals or the same terms of elements/components/steps may refer to the related description.

The following embodiments will illustrate a system and a method for diet management based on image analysis. As the risk of getting gastrointestinal diseases and cardiovascular diseases increases, diet management is an important issue in self-health management. In order to popularize and enhance the concept of diet management, a handheld device such as a smart phone may be incorporated with the system and the method for diet management in the embodiments hereinafter so as to reduce tedious record-filling steps and increase the willingness of usage. A user may capture images of daily diet and upload them to the system for diet management in the embodiments hereinafter via a smart phone. The content of diet images of the user may be analyzed in real time by the provided system and method for diet management. By a comparison technique on diet image series and population information, the system for diet management in the embodiments hereinafter not only provides the related information of a personal diet characteristic but also provides the population information that is much more similar to the personal diet content so as to assist the user to understand an outcome from the diet habit.

FIG. 1 is a flowchart of a computer-implemented method for diet management according to an embodiment of the present disclosure. Referring to FIG. 1, a supervector related to at least one diet image is provided in Step S110. In some embodiments, the diet image may be captured by a local device/system; in other embodiments, the diet image may be captured by a remote device/system. In some embodiments, the supervector may be generated through image analysis, image region segmentation and/or feature extraction on the diet image in Step S110. In some other embodiments, the supervector may be generated through image analysis and/or feature extraction on the whole diet image in Step S110. In some embodiments, the image analysis, the image region segmentation and/or the feature extraction may be performed by a local device/system; in some other embodiments, the image analysis, the image region segmentation and/or the feature extraction may be performed by a remote device/system such as a server.

In the present embodiment, a training model-based diet region segmentation method may be adapted in Step S110. For example, colors of common food may be defined, or segmentation training may be performed on collected training diet images to obtain a color distribution range of different types of food. The obtained color distribution range of different types of food may be a basis for diet region segmentation.

In the present embodiment, via collecting multiple types of food, characteristics of the common types of food are analyzed and concluded. As diet features with texture length, orientation, and/or complexity measurement are developed according to the characteristics, a coded statistical diagram based on the texture length, the orientation, and/or the complexity within the diet region may be set as a feature vector. The concluded diet image characteristics may be extracted in a flow of feature extraction in the present embodiment, wherein the flow will be described in detail later. In other embodiments, based on a design requirement of an actual product, the feature extraction in Step S110 may adapt a local binary pattern (LBP) algorithm, a scale invariant feature transformation (SIFT) algorithm, a speeded up robust features (SURF) algorithm, a histogram of orientation (HoG) algorithm, a RGB-LBP algorithm, an opponent-LBP algorithm, an nRGB-LBP algorithm, a RGB-SIFT algorithm or other image feature extraction algorithms, wherein the LBP algorithm, the SIFT algorithm, the SURF algorithm, the HoG algorithm, the RGB-LBP algorithm, the Opponent-LBP algorithm, the nRGB-LBP algorithm, and the RGB-SIFT algorithm are known techniques and will not be described hereinafter.

Figure 2:
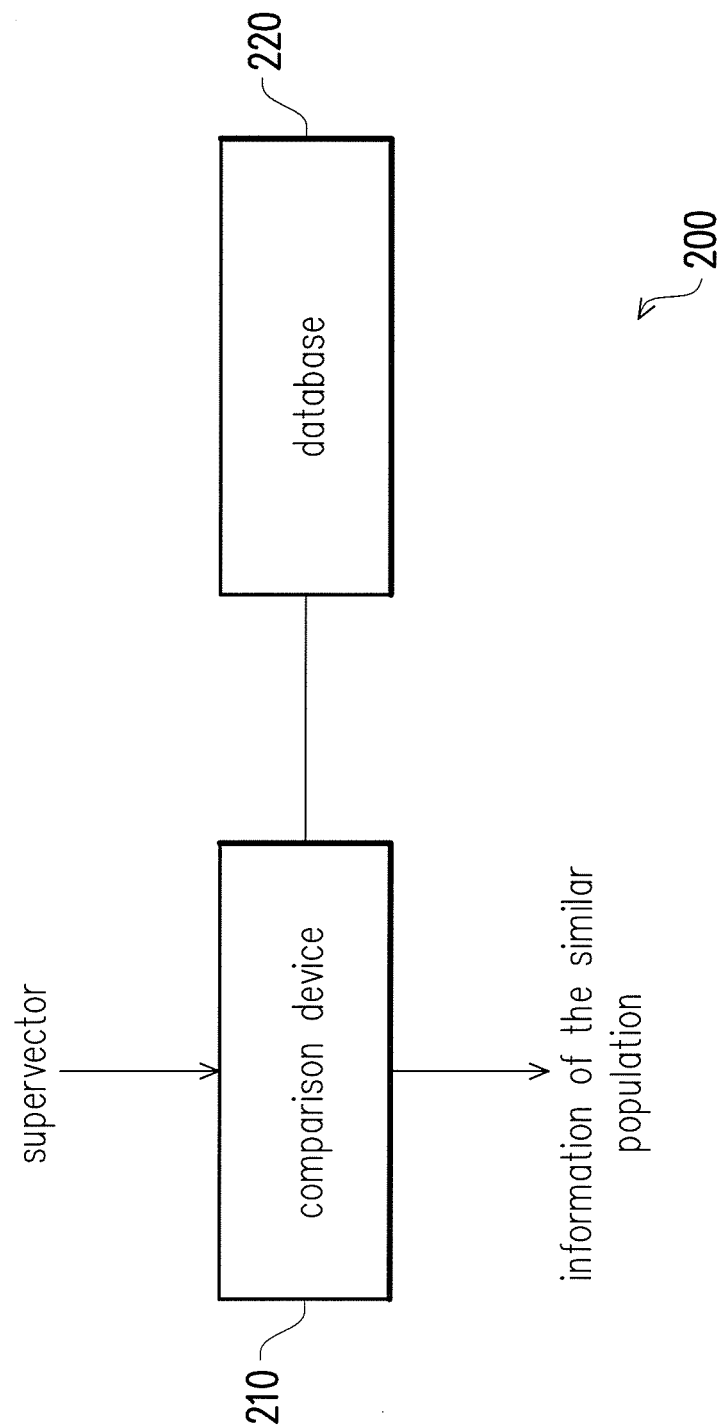
FIG. 2 is a functional block diagram of a system for diet management according to an embodiment of the present disclosure.

FIG. 2 is a functional block diagram of a system for diet management 200 according to an embodiment of the present disclosure. Based on a design requirement of an actual product, in some embodiments, the system for diet management 200 in FIG. 2 may be embodied as a handheld device, a desktop device, a stationary device, or other electronic devices. In other embodiments, the system for diet management 200 in FIG. 2 may also be embodied as an electronic system including a plurality of electronic devices. The system for diet management 200 includes a comparison device 210 (e.g. comparison circuit) and a database 220, wherein the comparison device 210 is coupled to the database 220. Referring to both FIG. 1 and FIG. 2, the comparison device 210 performs similarity comparison in the database 220 based on the supervector so as to find out at least one similar population in Step S120. The so-called "similarity comparison" may be realized in any method based on a design requirement of different actual systems. For example, a similarity between two diet images is calculated by adapting an integrated region matching method combined with an image region matching method in the present embodiment. Moreover, such concept may be extended to a diet image series so that a daily diet image series is provided to a user for performing similarity comparison with other users' diet image series, wherein the method will be described in detail later.

Next, the comparison device 210 provides information related to the similar population in Step S130. In some embodiments, the comparison device 210 may provide the information related to the similar population to the user in Step S130; in some other embodiments, the comparison device 210 may also provide the information to other devices such as a remote device/system and/or a local device/system in Step S130. The system for diet management 200 may compare the daily diet image series of the user with those of other users and return information of a population with a similar diet habit so as to assist the user to understand an outcome of such diet habit for self-health management.

Figure 3:
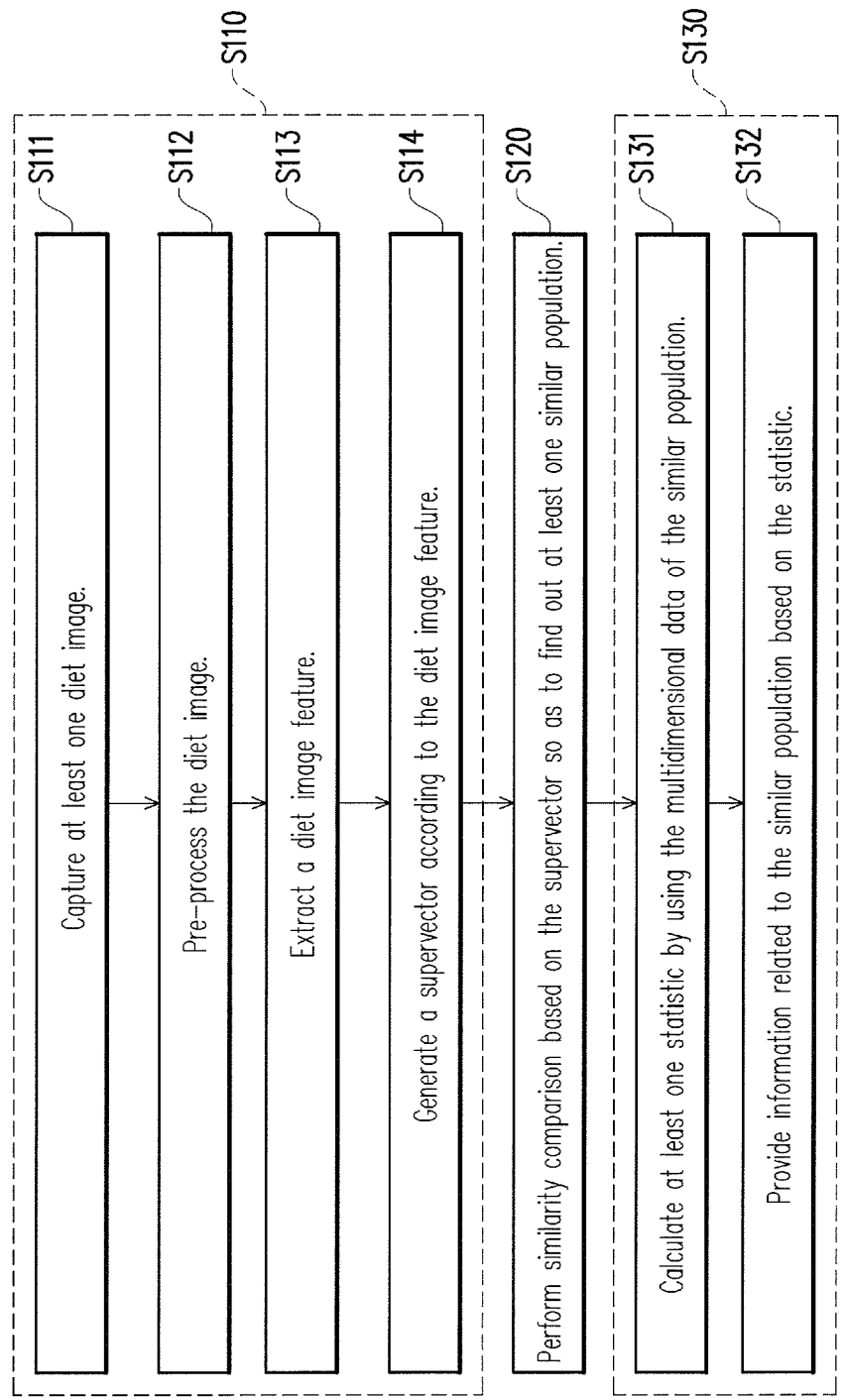
FIG. 3 is a flowchart of a method for diet management according to another embodiment of the present disclosure.

FIG. 3 is a flowchart of a computer-implemented method for diet management according to another embodiment of the present disclosure. The embodiment in FIG. 3 may refer to the related description in FIG. 1. The difference from the embodiment in FIG. 1 is that Step S110 includes Steps S111-S114 and Step S130 includes Steps S131-S132 in the embodiment in FIG. 3.

Figure 4:
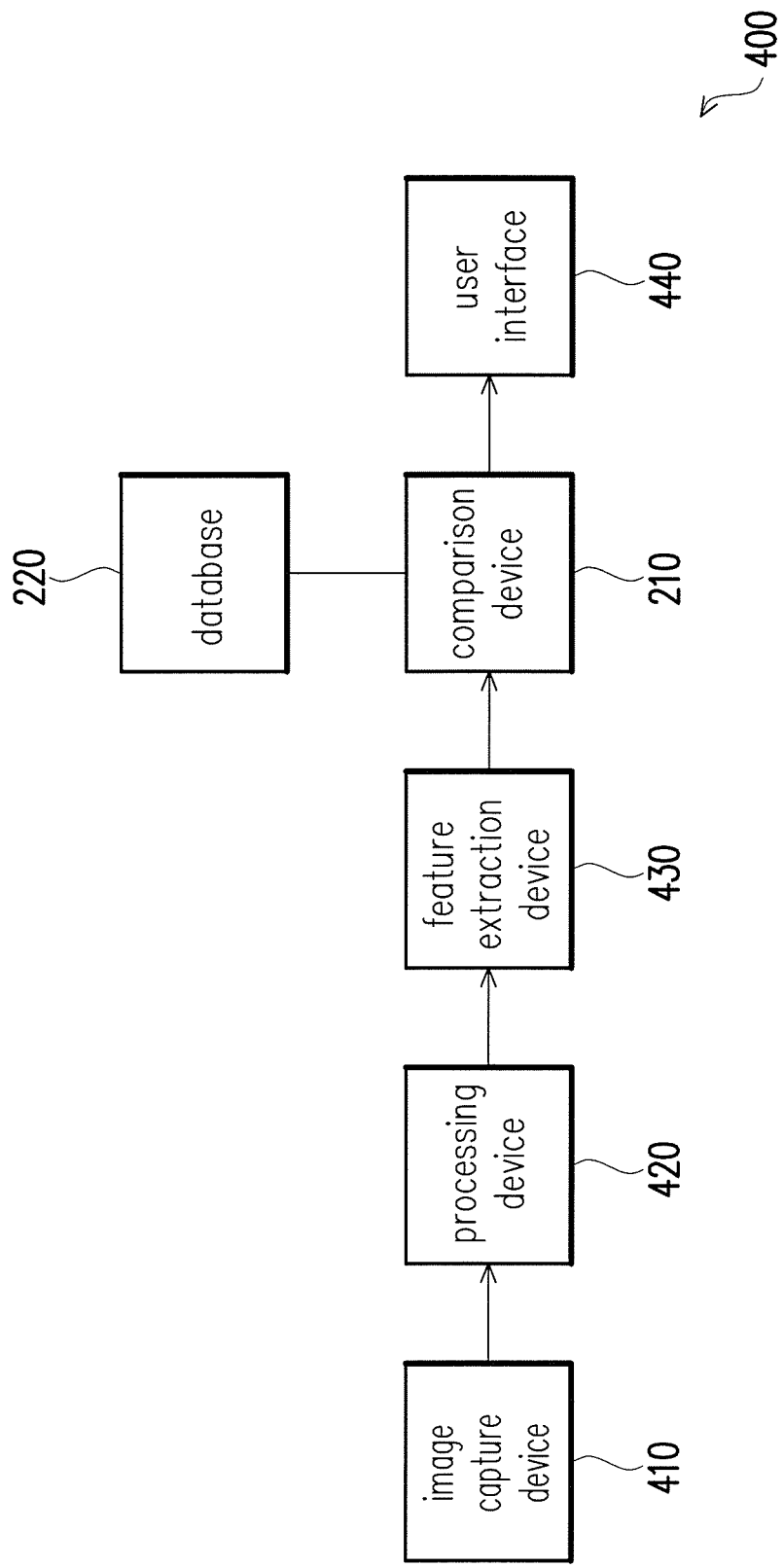
FIG. 4 is a functional block diagram of a system for diet management according to another embodiment of the present disclosure.

FIG. 4 is a functional block diagram of a system for diet management 400 according to another embodiment of the present disclosure. The embodiment in FIG. 4 may refer to the related description in FIG. 2. Based on a design requirement of an actual product, the system for diet management 400 in FIG. 4 may be embodied as a handheld device, a desktop device, a stationary device, or other local electronic devices. The difference from the embodiment in FIG. 2 is that an image capture device 410, a processing device 420 (e.g. processing circuit), a feature extraction device 430 (e.g. feature extraction circuit), and an interface 440 are included in the embodiment in FIG. 4. Based on a design requirement of the actual product, the user interface 440 may include a display, a light signal, a speaker, a microphone, and/or other output (or input) devices. Additionally, all or some of the processing device 420, the feature extraction device 430, and the comparison device 210 may be integrated to a single chip such as a micro-processor, a digital signal processor (DSP) or other control/processing circuits in other embodiments.

Referring to FIG. 3 and FIG. 4, the image capture device captures one or a plurality of diet images in Step S111. For example, before the user starts having a meal, the user may operate the system for diet management 400 such as a smart phone to capture an image of the meal so as to obtain the diet image.

The processing device 420 is coupled to the image capture device 410. The processing device 420 pre-processes the diet image in Step S112. In some embodiments, the diet image is transformed to a normalized space to reduce incompatibility between a tested image and images in the database in Step S112. In some other embodiments, the processing device 420 may remove a background of the diet image so as to obtain one or a plurality of diet regions from the diet image in Step S112. For example, the processing device 420 may perform image analysis on the whole diet image to obtain features of the diet image in the diet regions in Step S112 in some embodiments. For example, in some other embodiments, the pre-processing of the diet image includes color correction, brightness correction, and/or white balance correction as well as obtaining the diet regions by removing the background of the corrected diet image. In some embodiments, a graph-cut method, a grab-cut method or other algorithms may be adapted for image segmentation in Step S112. In the present embodiment, in terms of extraction and segmentation of the diet regions, the original diet image captured by the user is mainly segmented into one or a plurality of the diet regions based on color, texture, and/or other information for follow-up analysis processes specific to each of the diet regions.

For example, the processing device 420 may also segment the diet regions into one or a plurality of detailed food segments in Step S112. Take a diet image of a dish of steak as an example. The processing device 420 may segment out diet regions by removing a background and a dish from the diet image. Then, the processing device 420 may segment out the detailed food segment such as a steak or vegetables (if existed) from the diet regions.

Diet region segmentation is performed by a training model based on a Gaussian mixture model (GMM) using color (e.g. green, red, yellow, white, and black) as information in the present embodiment. Color types may be determined by each pixel of the diet image. The Gaussian mixture model is constructed based on information on greyscales, RGB, HSV or YIQ of foreground objects and background objects. Compared to a segmentation result from a conventional graphic-cut method, the method may not easily result in more and complicated detailed fractal information in the present disclosure.

The feature extraction device 430 is coupled to the processing device 420. In Step S113, the feature extraction device 430 extracts at least one diet image feature from the each detailed food segments provided by the processing device 420. After the features are extracted from the detailed food segments, the features are stored as a diet feature vector. In other embodiments, the feature extraction performed in Step S113 includes the LBP algorithm, the SIFT algorithm, the SURF algorithm, the HoG algorithm, the RGB-LBP algorithm, the Opponent-LBP algorithm, the nRGB-LBP algorithm, the RGB-SIFT algorithm, and/or other image feature extraction algorithms. The diet image feature transformed from an image signal may reflect information useful in diet habit analysis. In different embodiments, the diet image feature may include image capturing time, image capturing location, diet color, texture complexity, reflectivity, or other information, wherein the texture complexity includes texture magnitude, texture orientation, texture length, texture amount, texture regularity, or other features. In terms of the characteristics of the diet image, the feature may mainly be the texture orientation of the diet image in the present embodiment. A related flowchart is illustrated in FIG. 5.

Figure 5:
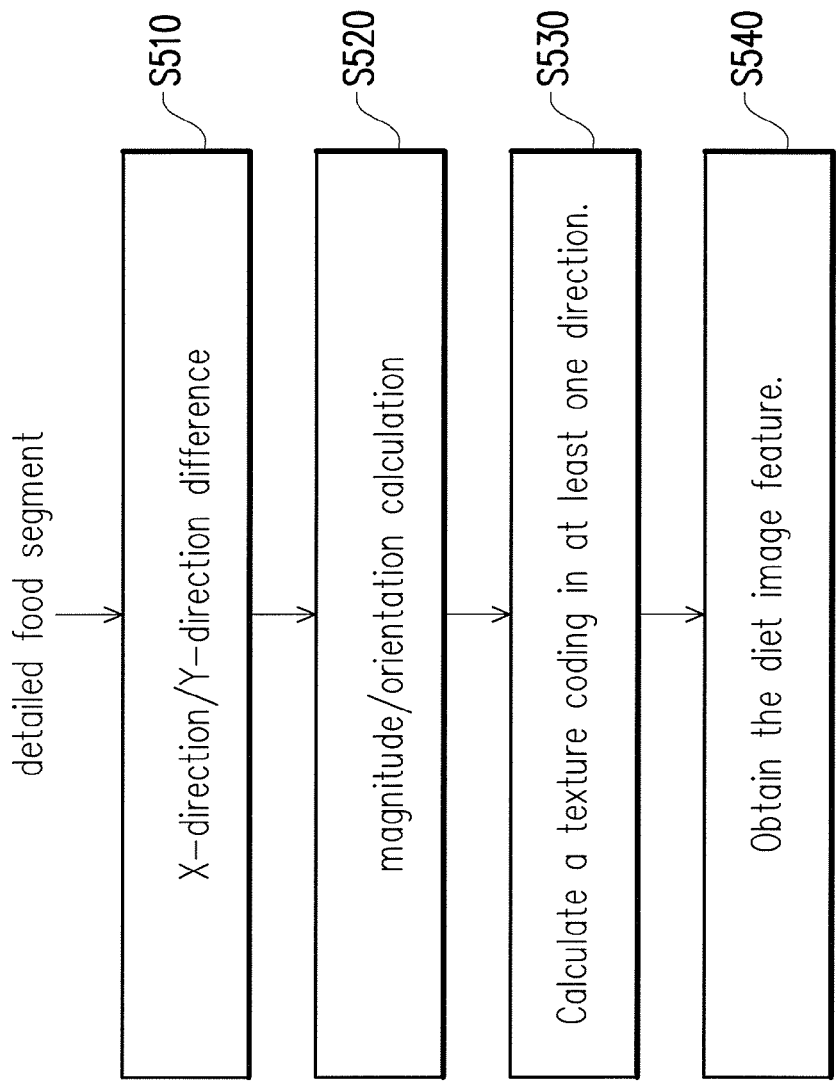
FIG. 5 is a flowchart of a method for feature extraction according to an embodiment of the present disclosure.

FIG. 5 is a flowchart of a computer-implemented method for feature extraction according to an embodiment of the present disclosure. Step S110 in FIG. 1 and Step S113 in FIG. 3 may refer to the related description in FIG. 5. The texture information of the image may be used as a basis for analysis through observation on food. Referring to FIG. 4 and FIG. 5, in Step S510, the feature extraction device 430 performs gradient operation on the detailed food segment by using first derivative gradient operators such as Roberts cross-gradient operators, Sobel operators, Prewitt operators for an X-direction difference calculation and a Y-direction difference calculation so as to obtain an X-direction difference image and a Y-direction difference image.

Figure 6:
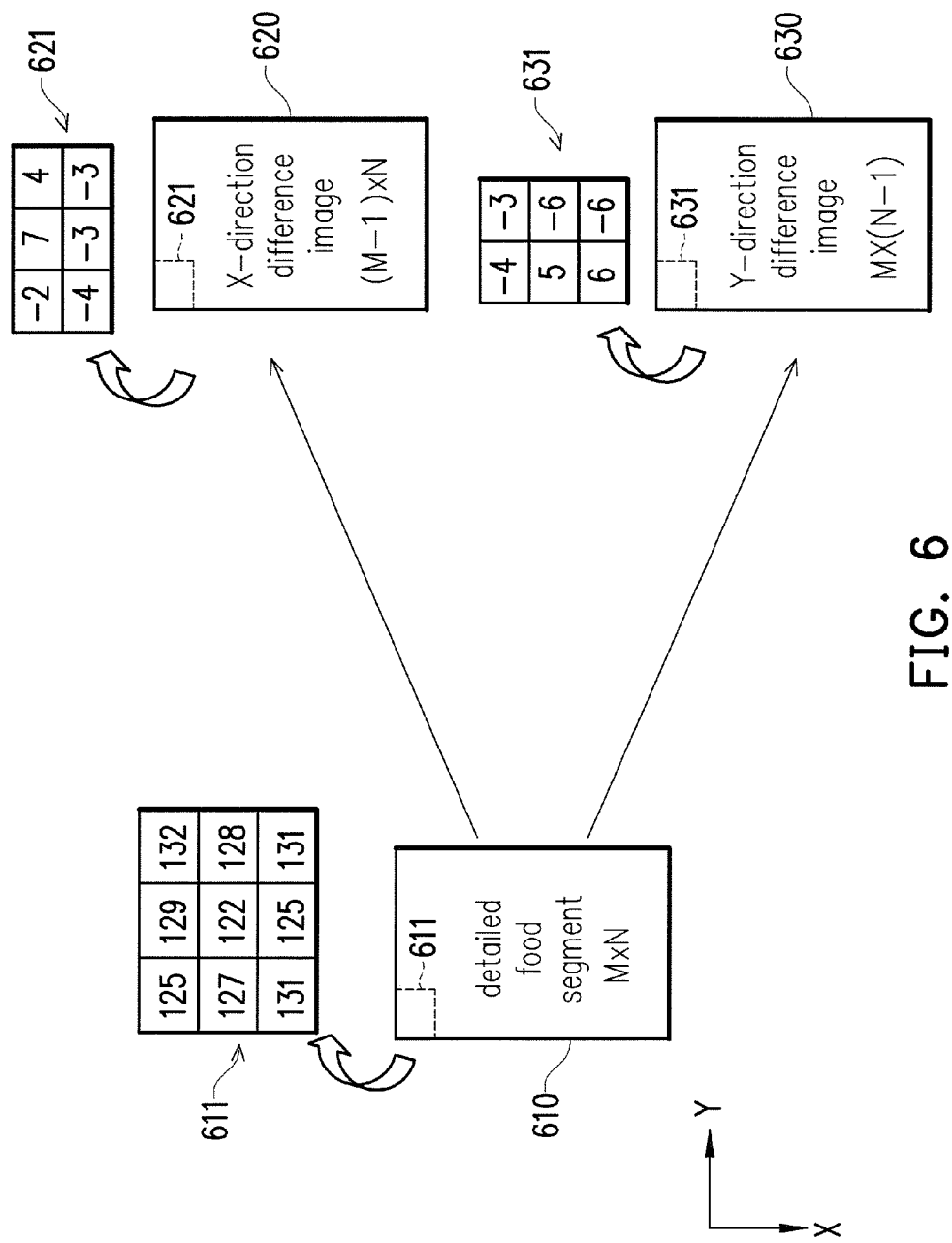
FIG. 6 is a schematic diagram of an X-direction difference calculation and a Y-direction difference calculation according to an embodiment of the present disclosure.

FIG. 6 is a schematic diagram of an X-direction difference calculation and a Y-direction difference calculation according to an embodiment of the present disclosure. A detailed food segment 610 represents a food segment cut from the diet image. It is noted that the shape of the detailed food segment 610 is not limited to a rectangle in FIG. 6. In an actual application, the detailed food segment 610 cut from the diet image is normally in an irregular shape.

In Step S510, the X-direction difference calculation is performed on the detailed food segment 610 so as to obtain an X-direction difference image 620. For example, in an X direction in FIG. 6, each pixel is subtracted by its neighboring pixels. Take a portion of pixels 611 in the detailed food segment 610 as an example. The upper-left pixel (with the value 125) of the portion of the pixels 611 subtracted by its neighboring pixel (the middle-left pixel of the portion of the pixels 611 with the value 127) obtains the X-direction difference −2. The X-direction difference −2 is the pixel value corresponding to the upper left pixel of a portion of the pixels 621 in the X-direction difference image 620. The other pixels may be performed in a similar fashion so as to obtain the X-direction difference image 620.

In Step S510, the Y-direction difference calculation may also be performed on the detailed food segment 610 so as to obtain a Y-direction difference image 630. For example, in a Y-direction in FIG. 6, each of the pixels is subtracted by its neighboring pixels. Take the portion of the pixels 611 in the detailed food segment 610 as an example. The upper-left pixel (with the value of 125) of the portion of the pixels 611 subtracted by its neighboring pixel (the upper-middle pixel of the portion of the pixels 611 with the value 129) obtains the Y-direction difference −4. The Y-direction difference −4 is the pixel value corresponding to the upper left pixel of a portion of the pixels 631 in the Y-direction difference image 630. The other pixels may be performed in a similar fashion so as to obtain the Y-direction difference image 630.

Referring to FIG. 4 and FIG. 5, the feature extraction device 430 calculates gradient magnitude information of the texture and gradient orientation information of the texture of each of the pixel points in the detailed food segment in Step S520. The gradient magnitude refers to a magnitude on an image boundary and the gradient orientation refers to an orthogonal direction of the image boundary (i.e. a normal direction, that is, the gradient and the boundary are orthogonal). Assume that the coordinate of a pixel is (x,y). Then texture magnitude information of the pixel is e(x,y) and texture orientation information of the pixel is θ(x,y). Formulas for calculating the texture magnitude information e(x,y) and the texture orientation information θ(x,y) may be expressed as Equation (1) and Equation (2), wherein $g_x$ represents the pixel value of the X-direction difference image at (x,y), $g_y$ represents the pixel value of the Y-direction difference image at (x,y), and $\tan^{-1}$ is an inverse tangent function.

$$e(x, y) = \sqrt{g_x^2 + g_y^2} \quad \text{Equation (1)}$$

$$\theta(x, y) = \tan^{-1}\left[\frac{g_y}{g_x}\right] \quad \text{Equation (2)}$$

The texture strength and texture orientation (i.e. boundary magnitude and orientation) of different diet types may be observed after a plurality of diet images of different diet types are processed by Step S510 and Step S520. Table 1 illustrates the texture characteristics presented from different diet types of diet images after processed by Step S510 and Step S520.

TABLE 1

Texture Characteristics of Different Diet Types

| Food | Boundary Length | Texture Amount | Regularity (Repetition) | Others |
| --- | --- | --- | --- | --- |
| Grain Class: white rice | N/A | Extremely less | With repetition if the texture is a lot. | |
| Grain Class: purple rice | Short | Extremely a lot | With repetition. | |
| Fruit Class: large and a lot | Long | Medium | With low repetition if the texture is a lot. | |
| Fruit Class: others | Short | Quite a lot | With repetition if the texture is a lot. | e.g. strawberries, grapes |
| Vegetable Class: light green | N/A/Long | Quite less | With low repetition | e.g. cabbages, Chinese cabbages |
| Vegetable Class: dark green | Long | Extremely a lot | With low repetition | |

Figure 7:
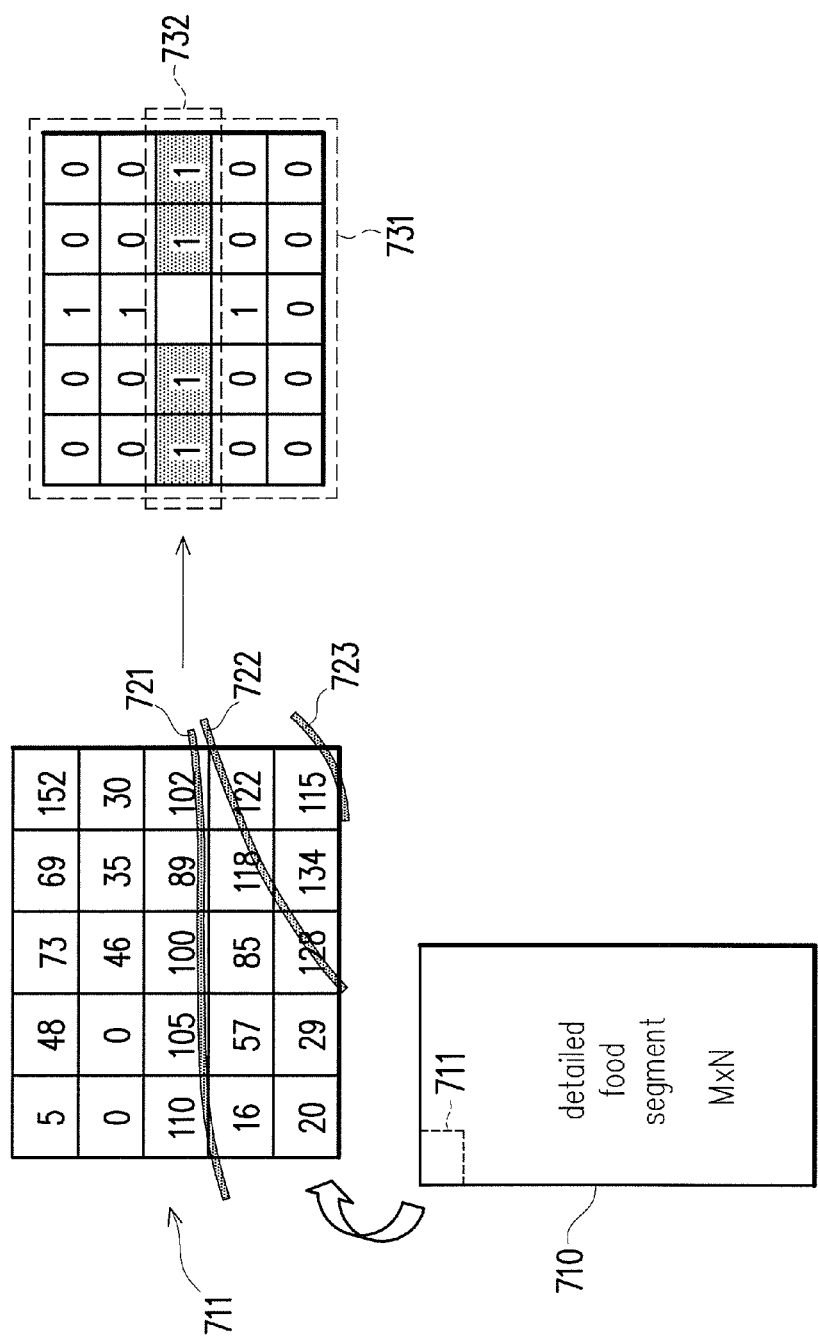
FIG. 7 is a schematic diagram of a texture coding calculation according to an embodiment of the present disclosure.

The feature extraction device 430 may calculate at least one texture coding in at least one direction in the detailed food segment by using the texture magnitude information e(x,y) and the texture orientation information θ(x,y) in Step S530. Analysis on the orientation information may be transformed to a form of parameters useable in value calculation analysis in Step S530. For example, FIG. 7 is a schematic diagram of a texture coding calculation according to an embodiment of the present disclosure. A detailed food segment 710 represents the texture orientation information of a food segment cut from the diet image. It is noted that the shape of the detailed food segment 710 is not limited to a rectangle in FIG. 7. In an actual application, the detailed food segment 710 cut from the diet image is normally in an irregular shape.

Referring to FIG. 7, take a portion of pixels 711 in a detailed food segment 710 as an example. Assume that the portion of the pixels 711 includes image boundaries 721, 722, and 723. After the aforementioned Step S510 and S520, the texture orientation information θ(x,y) of each of the portion of the pixels 711 is illustrated in FIG. 7. Since a tangential direction of the image boundary 721 is approximately horizontal (i.e. 0°), the texture orientation information θ(x,y) of the pixels on the image boundary 721 (i.e. the tangential direction or the normal direction of the boundary) are 110, 105, 100, 89, and 102. The feature extraction device 430 may select a target pixel one by one from the detailed food segment 710 to calculate texture coding in Step S530. For example, the feature extraction device 430 may select a target pixel (such as the central pixel of the portion of the pixels 711 with the value 100 as the texture orientation information θ(x,y)) from all of the pixels in the detailed food segment 710.

The feature extraction device 430 may perform binarization on the texture orientation information θ(x,y) of each of the pixels in the detailed food segment 710 so as to obtain a binary value D(x,y) of each of the pixels in the detailed food segment 710. Formulas for binarization are expressed as Equation (3) and Equation (4), wherein θi represents the texture orientation information θ(x,y) of the pixel at (x,y) in the detailed food segment 710, θn represents the angle of a normal vector in a direction to be observed, and $r_\theta$ represents an angle threshold value. θn and $r_\theta$ may be determined based on a design requirement of an actual product.

$$D(x,y)=1, \text{ if } |\theta i - \theta n| \le \gamma_\theta \quad \text{Equation (3)}$$

$$D(x,y)=0, \text{ if } |\theta i - \theta n| > \gamma_\theta \quad \text{Equation (4)}$$

Take the portion the pixels 711 in FIG. 7 as an example. Assume that the angle threshold value $r_\theta$ is 20°. Also, it is assumed that a direction to be observed is a horizontal direction (i.e. 0°); that is, the angle of a normal vector in the direction to be observed θn is 90°. In such conditions, the texture orientation information θ(x,y) of the upper left pixel in the portion of the pixels 711 (with the value 5) is converted to a binary value D(x,y)=0. The other pixels may be performed in a similar fashion so as to obtain the binary value D(x,y) of each of the pixels in the detailed food segment 710.

After the feature extraction device 430 selects a target pixel from the detailed food segment 710, the feature extraction device 430 may select a coding region or a patch along the direction to be observed in the detailed food segment 710, wherein the coding region includes the target pixel and a plurality of neighboring pixels. The size and the geometry shape of the coding region may be determined based on an actual design requirement. Considering differences among lengths on the boundary section of the diet image, masks designed accordingly with different sizes and orientations may reflect feature differences in the diet image. In terms of the diet image features in the present embodiment, orientation information of each pixel point of the image is the interested field in Step S530. For example, in some embodiments, the feature extraction device 430 may select a 5×5 matrix formed by the target pixel and two pixel points around the target pixel as a selected coding region (such as a coding region 731 in FIG. 7). The binary value D(x,y) of each pixel in the coding region 731 in FIG. 7 is converted from the texture orientation information θ(x,y) of the portion of the pixels 711, wherein the pixel without filling in the binary value D(x,y) is the selected target pixel. In some other embodiments, the feature extraction device 430 may select a 5×1 matrix formed by the target pixel and two pixels from the target pixel along the direction to be observed as the a coding region (such as a coding region 732 in FIG. 7).

Take the coding region 732 in FIG. 7 as an example. The number of neighboring pixels of the target pixel m is 4. When the feature extraction device 430 selects the central pixel (with the texture orientation information θ(x,y) 100) of the portion of the pixels 711 from all of the pixels in the detailed food segment 710 as the target pixel, the binary values D(x,y) of the neighboring pixels (with texture orientation information θ(x,y) 110, 105, 89, and 102) of the target pixel within the coding region 732 are 1, 1, 1, and 1 respectively. Next, the feature extracting device 430 may calculate category values bin and height values of the neighboring pixels. In the present embodiment, the feature extracting device 430 convert the binary value 1, 1, 1, and 1 of the neighboring pixels to the category value bin of the target pixel and determine the height value of the target pixel based on texture magnitude information e(x,y) of the target pixel. However, the calculation method for the height value is not limited to the aforementioned embodiment. For example, in some other embodiments, the feature extraction device 430 may select a constant (such as 1 or other real numbers) as the height value of the target pixel.

A formula for converting the binary values of the neighboring pixels to the category value bin of the target pixel may be expressed as Equation (5), wherein m represents the number of the neighboring pixels, and D(t) represents the binary value of the $t^{th}$ neighboring pixel. Therefore, the feature extracting device 430 may convert the binary values of the neighboring pixels to a decimal value. Take the coding region 732 in FIG. 7 as an example. The category value of the target pixel is bin=1+$2^3$*1+$2^2$*1+$2^1$*1+$2^0$*1=16.

$$bin = 1 + \sum_{t=1}^{m} 2^{m-t} \times D(t) \quad \text{Equation (5)}$$

The other pixels in the detailed food segment 710 may refer to the related description in FIG. 7 and Equations (3)-(5) and obtain the category value bin of each of the pixels in the detailed food segment 710 in a similar fashion. In the present embodiment, the feature extracting device 430 may set the texture magnitude information e(x,y) of the target pixel as the height value of the target pixel so as to obtain the height value of each of the pixels in the detailed food segment 710.

Figure 8:
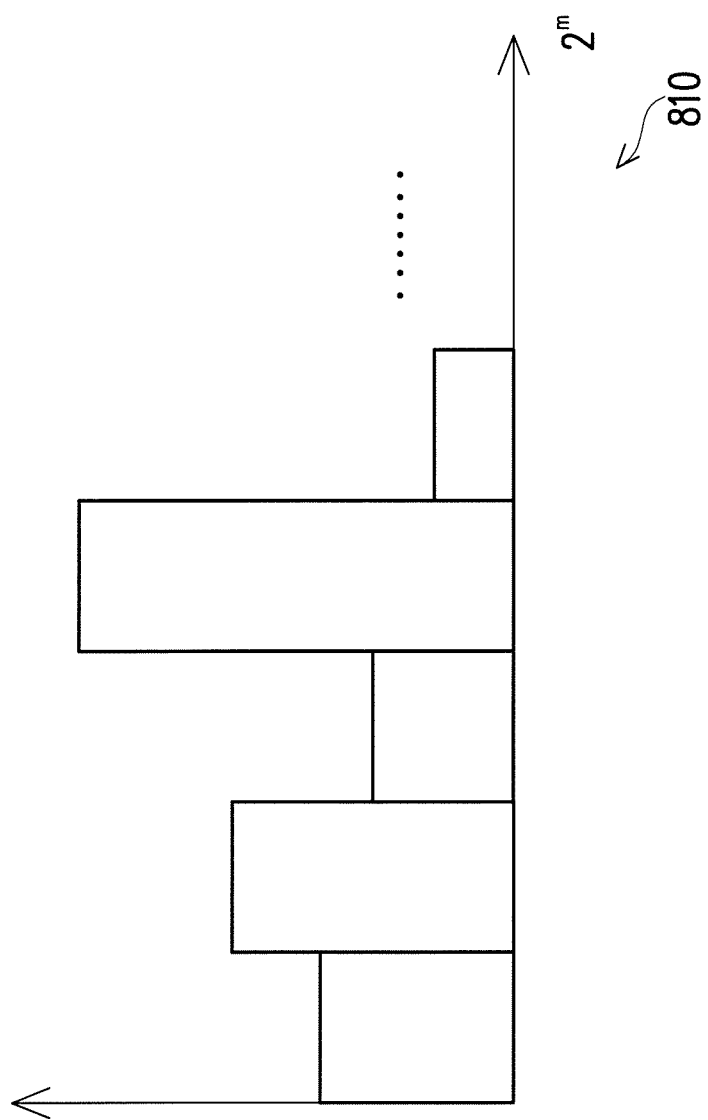
FIG. 8 is a schematic diagram of a histogram of the calculated height values such that the X-direction is set as the direction to be observed according to an embodiment of the present disclosure.

The feature extraction device 430 may determine the texture coding in the direction to be observed in the detailed food segment 710 based on the category values bin and the height values of all of the pixels in the detailed food segment 710 in Step S530. For example, among all of the pixels in the detailed food segment 710, the feature extraction device 430 may accumulate the height value (e.g. the texture magnitude information e(x,y)) of the pixels with the same category value (e.g. 16) so as to obtain a histogram. For example, FIG. 8 is a schematic diagram of a histogram of the calculated height values such that the horizontal direction is set as the direction to be observed according to an embodiment of the present disclosure. In FIG. 8, the horizontal axis of a histogram 810 represents the category values bin, and the vertical axis of the histogram represents the height values. The feature extraction device 430 may determine the texture coding in the direction to be observed in the detailed food segment 710 based on the histogram in Step S530. By that means, besides the texture amount and the regularity may be reflected, the information on the existence of longer connecting boundary (texture length) in the observed direction may be extracted. Such characteristic is an image texture characteristic unable to be presented by a conventional algorithm such as HoG characteristic parameters).

Referring to FIG. 4 and FIG. 5, the feature extraction device 430 integrate the texture coding in the direction to be observed so as to obtain the diet image feature in Step S540. In some embodiments, if the direction to be observed is a single direction such as a horizontal direction, the feature extraction device 430 may set a single histogram (such as the histogram in FIG. 8) to be the diet image feature of the detailed food segment 710 (i.e. the detailed food segment 610). However, the direction to be observed is not limited to the horizontal direction. In other embodiments, the feature extraction device 430 may perform the related operations in FIG. 5 to FIG. 8 on the detailed food segment 610 (the detailed food segment 710) in a plurality of different directions to be observed so as to obtain a plurality of histogram (texture coding) corresponding to the different directions. Therefore, the feature extraction device 430 may integrate the texture coding corresponding to the different directions so as to obtain the diet image feature in Step S540. In the present embodiment, the feature extraction device 430 may connect a plurality texture coding corresponding to different directions to each other in a preset connection order so as to obtain the at least one diet image feature of the detailed food segment. The connection order may determine by an actual design requirement.

Figure 9:
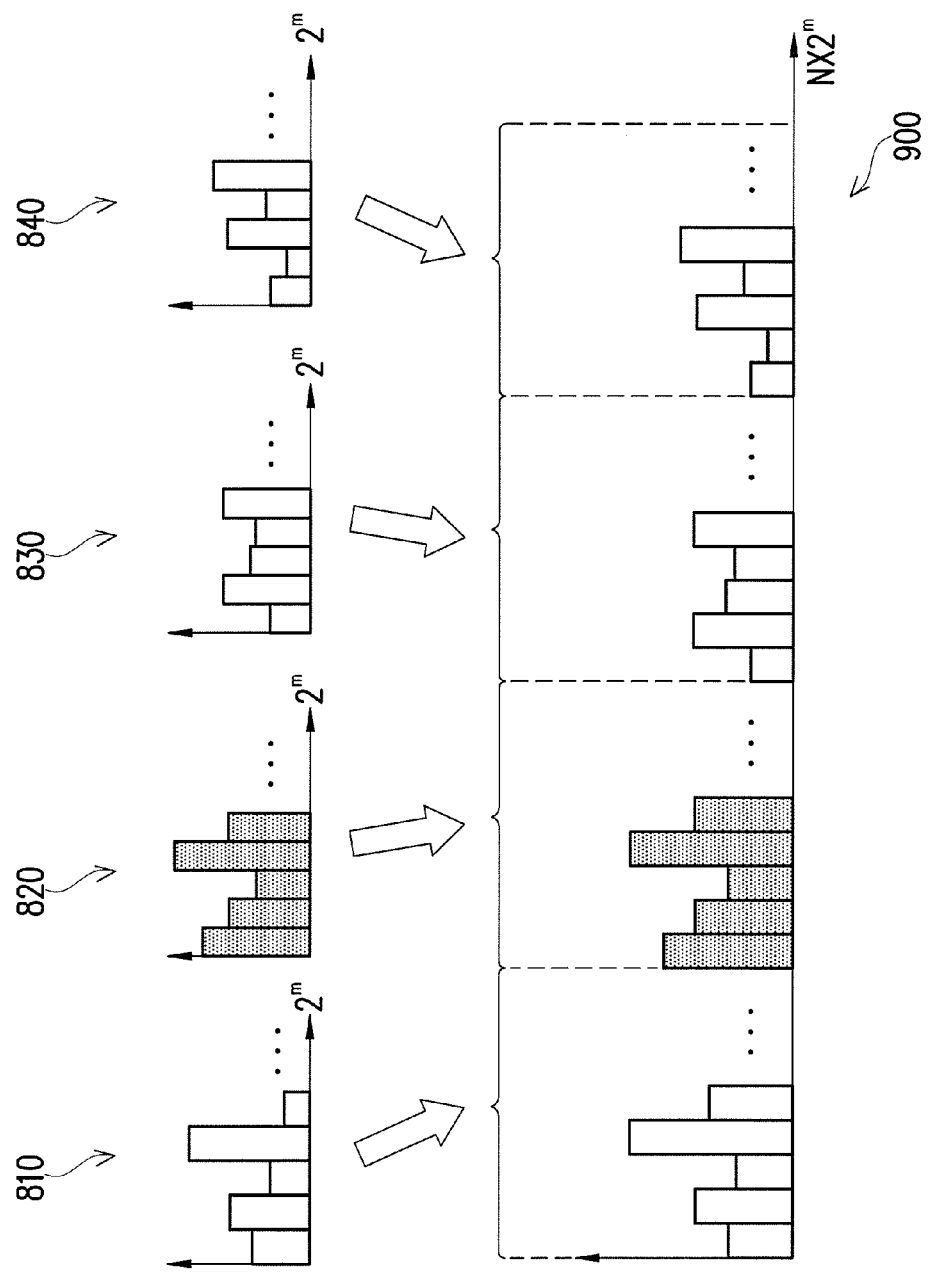
FIG. 9 is a schematic diagram of histograms of the calculated height values such that a plurality of different directions are set as the direction to be observed according to an embodiment of the present disclosure.

For example, the feature extraction device 430 may perform the related operation in FIG. 5 to FIG. 8 in a horizontal direction (i.e. 0°), a vertical direction (i.e. 90°, a right-tilt direction (i.e. 45°), and a left-tilt direction (i.e. 135°) so as to obtain a plurality of histograms corresponding to different directions. FIG. 9 a schematic diagram of histograms of the calculated height values such that a plurality of different directions are set as the directions to be observed according to an embodiment of the present disclosure. In FIG. 9, the horizontal axis of histograms represents the category value bin, and the vertical axis of histograms represents the height value. Histograms (texture coding) 810, 820, 830, and 840 are obtained by performing the related operation in FIG. 5 to FIG. 8 in the horizontal direction (i.e. 0°), the vertical direction (i.e. 90°), the right-tilt direction (i.e. 45°), and the left-tilt direction (i.e. 135°). In the present embodiment, the feature extraction device 430 may connect the histogram 810-840 (texture coding) to each other in a [0°, 90°, 45°, 135°] connection order so as to form a histogram 900 (i.e. the diet image feature of the detailed food segment 610). If the number of the neighboring pixels m in Step S530 is 4, the histograms 810-840 in each of the directions include 16 category values bin. Since the histogram in each of the directions includes 16 bin, the histogram 900 may include 16×4=64 bins eventually. The histogram 900 including 64 bins may arrange the height value of each of the bins to a 64-dimensional vector, which is used for representing the feature of the diet image/segment characteristic in the present embodiment.

In other embodiments, the feature extraction device 430 may connect the histogram 810-840 (texture coding) to each other in other connection order (such as in a [0°, 45°, 90°, 135°] order or other orders) so as to form the diet image feature of the detailed diet segment 610.

To sum up, the feature extraction device 430 may calculate an X-direction and a Y-direction image signal differences and further calculate gradient magnitude and gradient orientation (angle) information, wherein the one with high gradient energy represents that the pixel point is an obvious boundary and the gradient orientation information may provide the texture orientation. After the magnitude is standardized, the feature extraction device 430 may code the feature information in different directions to a value for a coding region (or patch) corresponding to each of the pixels and the gradient energy magnitude $e(x,y)$ corresponding to each of the pixels is set to be a weight-adjusted basis (i.e. the boundary of the diet image affecting the diet image parameter is adjustable). Lastly, a statistical histogram calculated from an accumulation of each of the pixel points is set to be the diet image feature.

Referring to FIG. 3 and FIG. 4, the feature extraction device 430 generates a supervector to the comparison device 210 according to at least one diet image feature in Step S114. In some embodiments, if the diet image includes a single detailed food segment, the feature extraction device 430 may set the diet image feature in the single detailed food segment to be the supervector and further provide the supervector to the comparison device 210. In some embodiments, if the diet image includes a plurality of detailed food segments, the supervector provided to the comparison device 210 from the feature extraction device 430 may include diet image features in all of the detailed food segments.

In some other embodiments, the system for diet management 400 may define a diet recording period. The diet recording period may be constantly set in the system for diet management 400 or may be determined by the user. The user may operate the system for diet management 400 during the diet recording period for capturing images of diet contents during the diet recording period. The system for diet management 400 may perform the related process in Step S111 to Step S113 on a plurality of diet images capturing during the diet recording period so as to obtain a plurality of diet image features of different detailed food segments during the diet recording period. In the present embodiment, the feature extraction device 430 connects the diet image features of the plurality of diet images during the diet recording period to form the supervector in an order based on capturing time in Step S114. However, the connection order of the plurality of the image diet features within the supervector may not be restricted to the order of capturing time. In other embodiments, the plurality of the diet image features may be connected to the supervector in other orders (or even in any random order).

The diet recording period may be set in several days, several weeks, several months, or several years, and so on. The supervector may present the diet characteristic of the user during the diet recording period. By setting one to multiple groups of diet images captured during the diet recording period, follow-up diet characteristic analysis may be performed in a consistent standard, which further provide a better reference of the result of the analysis.

The system for diet management 400 may use a determined result from the feature extraction device 430 to perform a personal diet characteristic analysis. The diet image may exist different food characteristic such as Diet Pyramid (grains, vegetables, fruits, oils, meat and beans, and milk) defined by the Bureau of Health Promotion, the Department of Health, Taiwan (corresponding to MyPyramid defined by the United States Department of Agriculture in 2005), Health Plate (grains, vegetables, fruits, protein, and milks) (corresponding to My Plate defined by the United States Department of Agriculture in 2010), or the characteristics of Chinese traditional food in five elements and five colors (wood/green, fire/red, earth/yellow, gold/white, and water/black).

Referring to FIG. 3 and FIG. 4, the comparison device 210 performs similarity comparison between the supervector provided by the feature extraction device 430 and other people's supervectors in the database 220 so as to select at least one similar population in Step S120. The other people's supervectors include the diet characteristics of all the people excluding the user. For example, the database 220 includes 10,000 other people's data (including a supervector and multidimensional data of these people). The comparison device 210 finds out the top 100 similar supervectors with respect to the supervector from the 10,000 other people's supervectors provided by the feature extraction device 430 and defines the 100 other people's data as the similar population. As another example, in some other embodiments, the comparison device 210 may perform similarity comparison between the 10,000 other people's data and the supervector provided by the feature extraction device 430 respectively so as to obtain 10,000 other people's similarities corresponding to the 10,000 other people's data. The comparison device 210 may select/define the similar population from the other people's data having the other people's similarities within a preset threshold (e.g. with a similarity greater than 70%). In other embodiments, if the number of the other people's data in the similar population selected/defined by the comparison device 210 is not greater than a minimum preset number such as 30, the similar population may be invalid.

In some embodiments, in the situation in which the system for diet management 400 defines the diet recording period, the comparison device 210 may performs similarity comparison between the supervector provided by the feature extraction device 430 and all the other people's supervectors with the same duration as the diet recording period in the database 200 so as to select the similar population. In other embodiments, if the system for diet management 400 does not define the diet recording period, the comparison device 210 may perform similarity comparison between the supervector provided by the feature extraction device 430 and all of the other people's supervectors in the database 220 so as to select the similar population.

Figure 10:
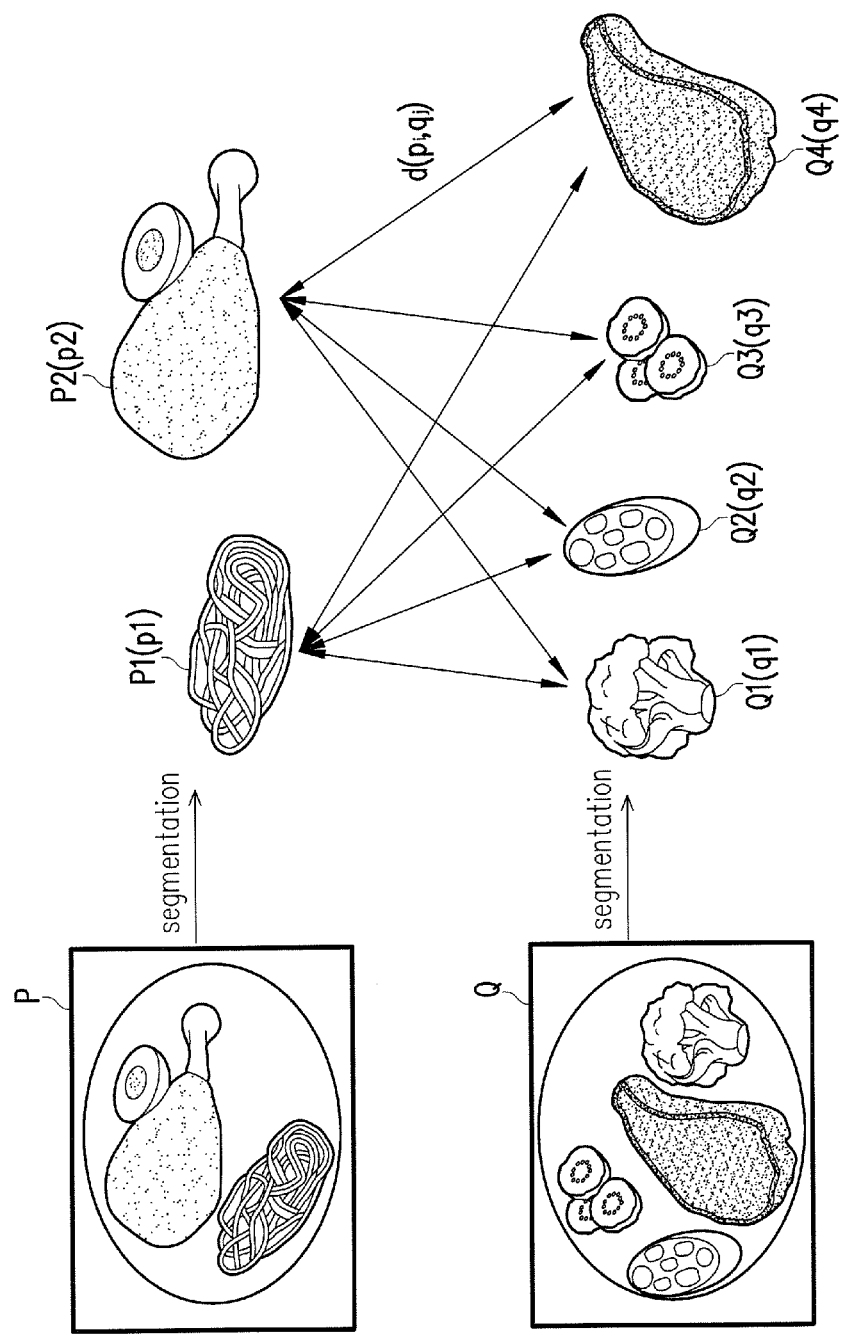
FIG. 10 is a schematic diagram of a system for diet management performing similarity comparison on diet image features according to an embodiment of the present disclosure.

FIG. 10 is a schematic diagram of a system for diet management performing similarity comparison on diet image features according to an embodiment of the present disclosure. A diet image P in FIG. 10 represents a diet image captured by the system for diet management operated by the user; that is, a diet content of the user. A diet image Q in FIG. 10 represents a diet image captured by another person. The image Q is pre-processed by the same method in Step S111 to S114 such that the image Q is segmented into detailed food segments Q1, Q2, Q3, and Q4, and diet image features q1, q2, q3, and q4 are extracted from the detailed food segments Q1-Q4 respectively. The diet image features q1-q4 of the another person are pre-stored in the database 220 to be a part of contents of the another person's supervector.

After the diet image P is processed by Steps S111 to S114, the diet image P is segmented into detailed food segments P1 and P2, and diet image features p1 and p2 are extracted from the detailed food segments P1 and P2 respectively. The comparison device 210 perform similarity comparison between the diet image features p1 and p2 of the supervector and the diet image features q1-q4 in the database 220 so as to calculate a similarity between the diet image P and the diet image Q in Step S120. The comparison device 210 may calculate a Euclidean distance, an angle, a correlation coefficient, or mutual information between the supervector representing the diet image P and the another person's supervector representing the diet image Q as well as consider percentage information of the detailed food segments in the diet images so as to obtain the similarity between the diet image P and the diet image Q. For example, the similarity comparison is performed between the diet image feature p1 and the diet image features q1-q4 so as to obtain distance values d(p1,q1), d(p1,q2), d(p1,q3), and d(p1,q4). The similarity comparison is performed between the diet image feature p2 and the diet image features q1-q4 so as to obtain distance values d(p2,q1), d(p2,q2), d(p2,q3), and d(p2,q4). The distance values d(p1,q1), d(p1,q2), d(p1,q3), d(p1,q4), d(p2,q1), d(p2,q2), d(p2,q3), and d(p2,q4) are integrated and the percentage information of each of the detailed food segments in the diet images are considered so as to obtain the similarity between the diet image P and the diet image Q.

For example, in some embodiments, the comparison device 210 may calculate a significance of region pair S(i,j) between every two of the detailed food segments by an integrated region matching (IRM) algorithm, wherein S(i,j) represents the percentage information of the food segments Pi or Qj in the diet images P and Q. The principle is as follows. First, the distance of the diet feature vector of each of the every two food segments (Pi,Qj) is calculated. Next, the pairs with the nearest distance may be assigned the significance of region pair S(i,j). Lastly, according to the significance of region pair S(i,j), the distance of each of the every two food segments $d(P,Q)=\Sigma_{i,j}S(i,j)d(p_i,q_j)$ may be calculated; that is, the similarity between the diet image P and the diet image Q is obtained. Such algorithm may be extended to similarity comparison among image series of a plurality of diet images.

Referring to FIG. 3 and FIG. 4, in Step S131, the comparison device 210 may calculate at least one statistic of the similar population from the multidimensional data of the similar population found in Step S120. The multidimensional data includes age, gender, weight, residency, occupation type, diet time, physical health status, mental health status, and/or disease development status. The statistics of the similar population includes demographic data, personal health statistical data, diet time statistical data or other statistical data of the similar population. The demographic data includes characteristics of age distribution, percentage of gender distribution, characteristics of weight distribution, characteristics of occupation type, or other statistical data. The personal health statistical data includes historical disease, medical information, current disease status, current physical and mental status or other related information.

For example, the comparison device 210 may obtain the age data of the similar population from the database 220. The comparison device 210 may obtain the age distribution of the population which is the most similar to the user in diet habit/characteristic. As another example, the comparison device 210 may obtain the occupation data of the similar population from the database 220. The comparison device 210 may obtain the job distribution of the population which is the most similar to the user in diet habit/characteristic. As another example, the comparison device 210 may obtain the disease status data of the similar population from the database 220. The comparison device 210 may obtain the disease distribution of the population which is the most similar to the user in diet habit/characteristic.

In Step 132, the comparison 210 may provide the information related to the similar population based on the statistic of the similar population found in Step S131. In some embodiments, the comparison device 210 may provide the information related to the similar population to the user via the user interface 440. In some other embodiments, in Step S132, the comparison device 210 may also provide the information related to the similar population to other devices such as a remote device/system and/or another local device/system via a communication network.

Therefore, the diet managements system 400 in the present embodiment may record diet images of one day or multiple days and connect the diet images to a supervector in a time order. The supervector may be compared with all the other people's supervectors in the database 220 so as to find out a population which is the most similar to the user in the diet characteristics. In the present embodiment, the system for diet management 400 may analyze the multidimensional population information statistically from the population which is the most similar to the user in the diet characteristics so as to provide a possible outcome from the current diet habit to the user. In other embodiments, after the similar population is found, the supervector and the multidimensional data of the user may be added to the database 220 for other people to do the searching.

In the present embodiment, the multidimensional data of at least one non-similar population is used for calculating at least one statistic of the non-similar population, and the statistics between the similar population and the non-similar population are compared so as to provide a comparison result to the user, the remote device and/or the another local device in Step S132. In some embodiments, the non-similar population refers to the related data excluding the similar population. In some other embodiments, the non-similar population refers to all of the related data in the database 220 (including the similar population). In the present embodiment, in Step S132, categories of the information with significant difference between the statistics of the similar population and the non-similar population are found by using a data mining technique and/or a statistical test and are set to be the diet habit characteristic of the similar population, wherein the diet habit characteristic of the similar population is provided to the user.

Figure 11:
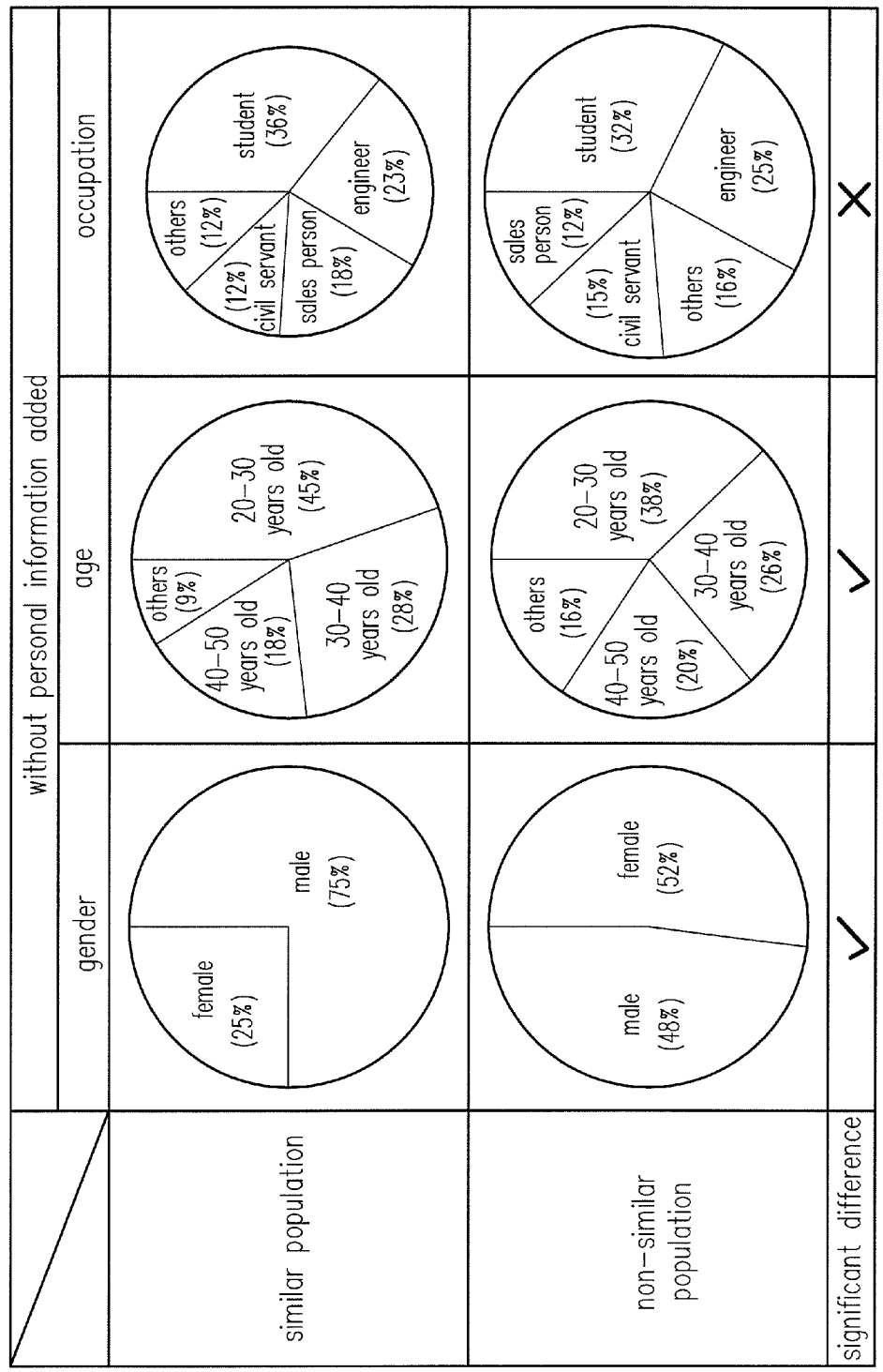
FIG. 11 is a schematic diagram of significant differences between the statistics of a similar population and a non-similar population according to an embodiment of the present disclosure.

For example, FIG. 11 is a schematic diagram of significant differences between the statistics of a similar population and a non-similar population according to an embodiment of the present disclosure. Referring to FIG. 11, since the percentage of the males is 75% in the similar population and percentage of the males is 48% in the non-similar population, it represents that the statistic of the similar population (the statistic of the gender) is significantly different. The occupation distribution of the similar population and the distribution of the non-similar population in FIG. 11 are not much different. It represents that the statistic of the similar population (the statistic of the occupation) is not significantly different.

Figure 12:
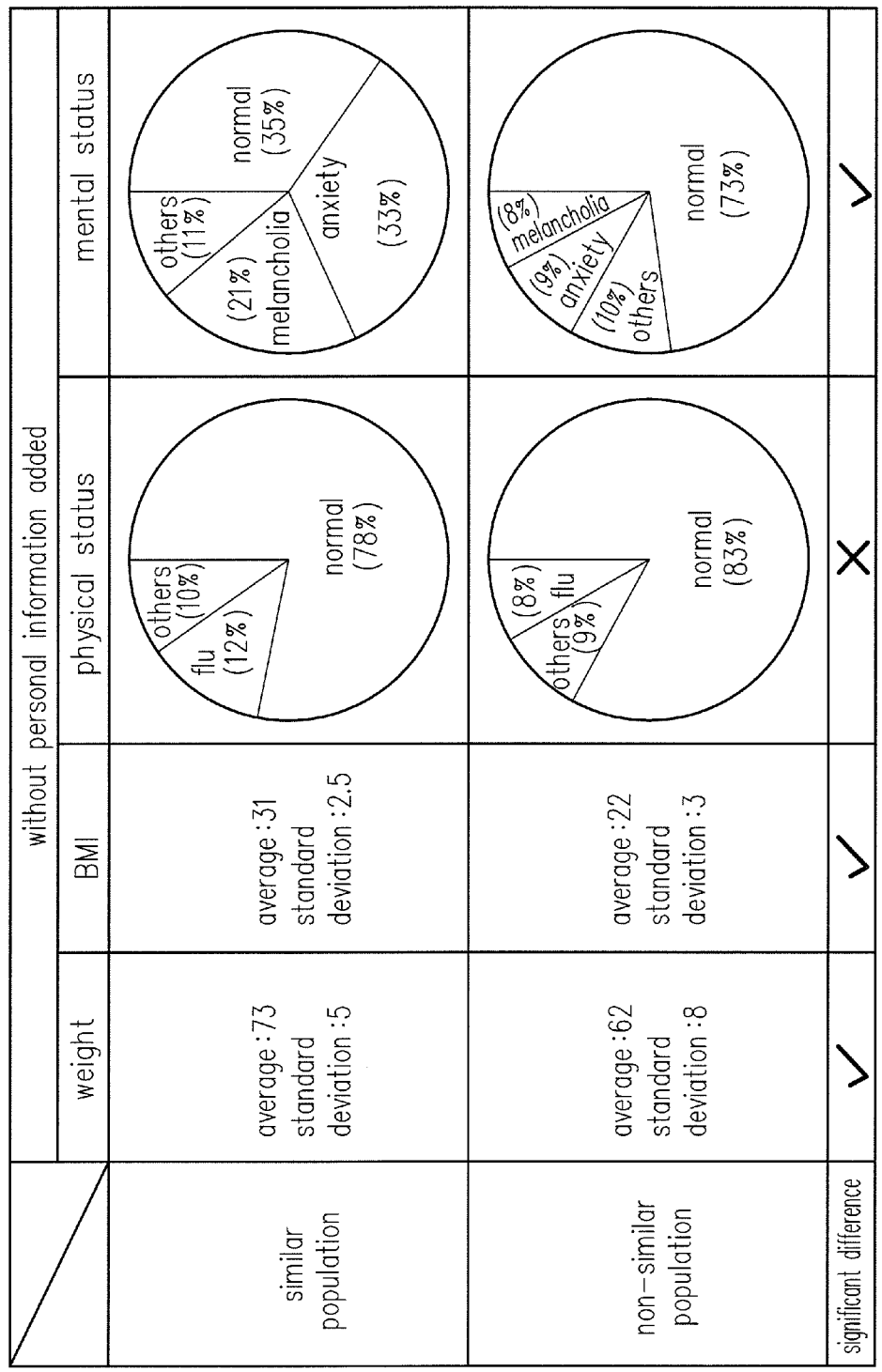
FIG. 12 is a schematic diagram of significant differences between the statistics of a similar population and a non-similar population according to another embodiment of the present disclosure.

As another example, FIG. 12 is a schematic diagram of significant differences between the statistics of a similar population and a non-similar population according to an embodiment of the present disclosure. Referring to FIG. 12, since the distribution of the physical status of the similar population and that of the non-similar population are not much different, it represents that the statistic (the statistic of the physical status) of the similar population is not significantly different. In FIG. 12, since the average weight of the similar population is 73 kg (with the standard deviation 5 kg) and the average weight of the non-similar population is 62 kg (with the standard deviation 8 kg), it represents that the statistic (the statistic of the weight) of the similar population is significantly different. That is, the average weight of the population which is the most similar to the user in diet characteristic is significantly greater than the average weight of the non-similar population. The user may have a better idea on a possible outcome of the current diet habit through the significant difference between the statistics of the similar population and the non-similar population.

Figure 13:
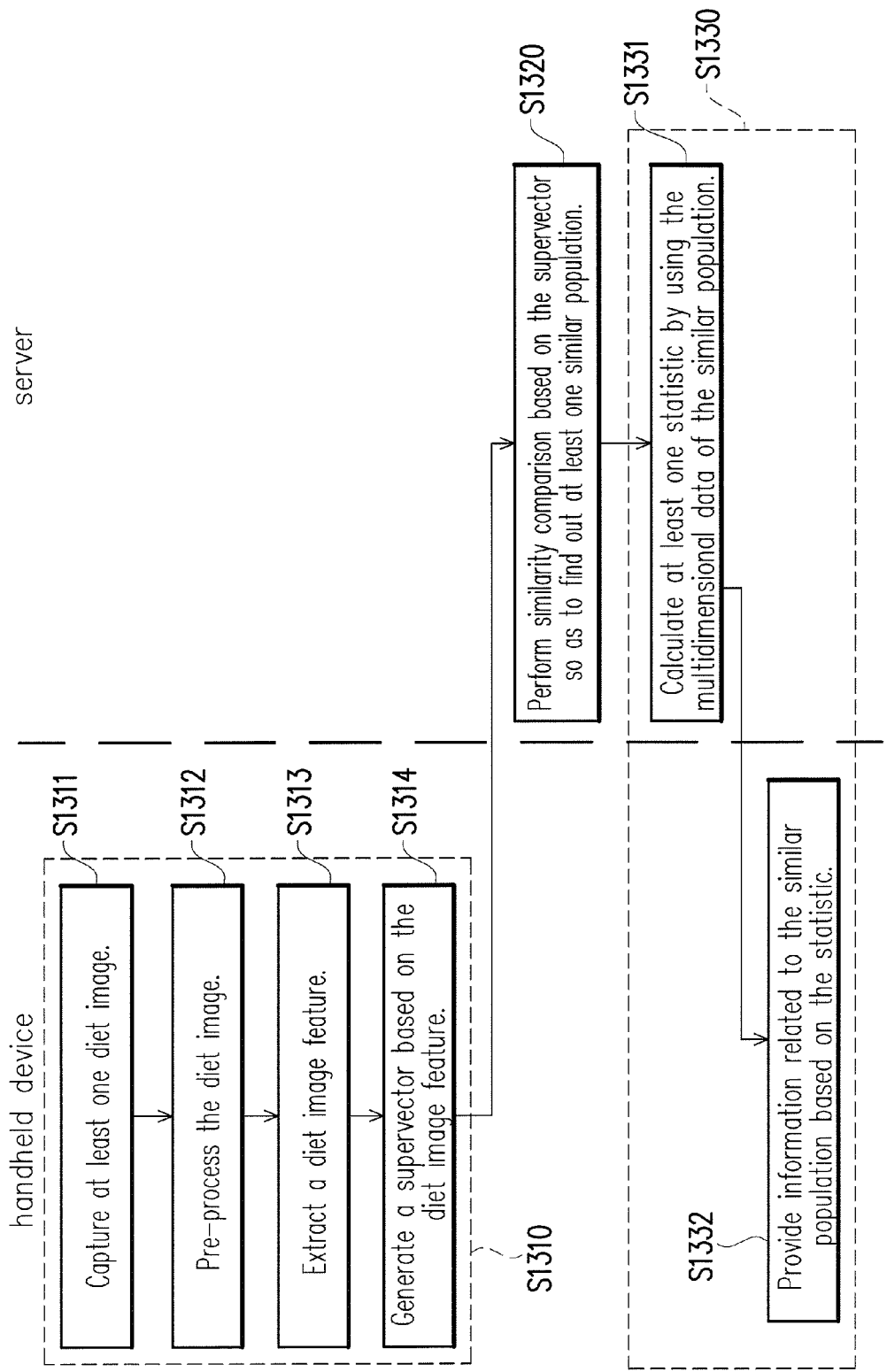
FIG. 13 is a flowchart of a method for diet management according to another embodiment of the present disclosure.

FIG. 13 is a flowchart of a computer-implemented method for diet management according to another embodiment of the present disclosure. Steps S1310-S1330 of the embodiments in FIG. 13 may refer to the related description Steps S110-S130 in FIG. 1 and FIG. 3. The only difference from the embodiment in FIG. 3 is that Steps S1311, S1312, S1313, S1314, and S1332 in FIG. 13 are executed by a handheld device while Steps S1320 and S1331 are executed by a server.

Referring to FIG. 13, the handheld device captures at least one diet image via an image capture device (Step S1311). The handheld device pre-processes the at least one diet image so as to segment out at least one diet region from the diet image and segment out at least one detailed food segment from the diet region (Step S1312). The handheld device extracts at least one diet image feature from the detailed food segment (Step S1313) and generates a supervector of the diet image feature (Step S1314). Steps S1311-S1314 of the embodiment in FIG. 13 may refer to the related description of Step S111-S114 in FIG. 3 and may be performed in a similar fashion. The handheld device uploads the supervector related to the diet image to the server. The server performs similarity comparison in a database based on the supervector so as to find out at least one similar population in Step S1320. The server provides the related statistical information of the similar population to the handheld device (Step S1331). The handheld device receives the information related to the similar population from the server and provides the information related to the similar population to the user (Step S1332). Steps S1331-S1332 of the embodiment in FIG. 13 may refer to the related description in Steps S131-S132 in FIG. 3 and may be performed in a similar fashion.

Figure 14:
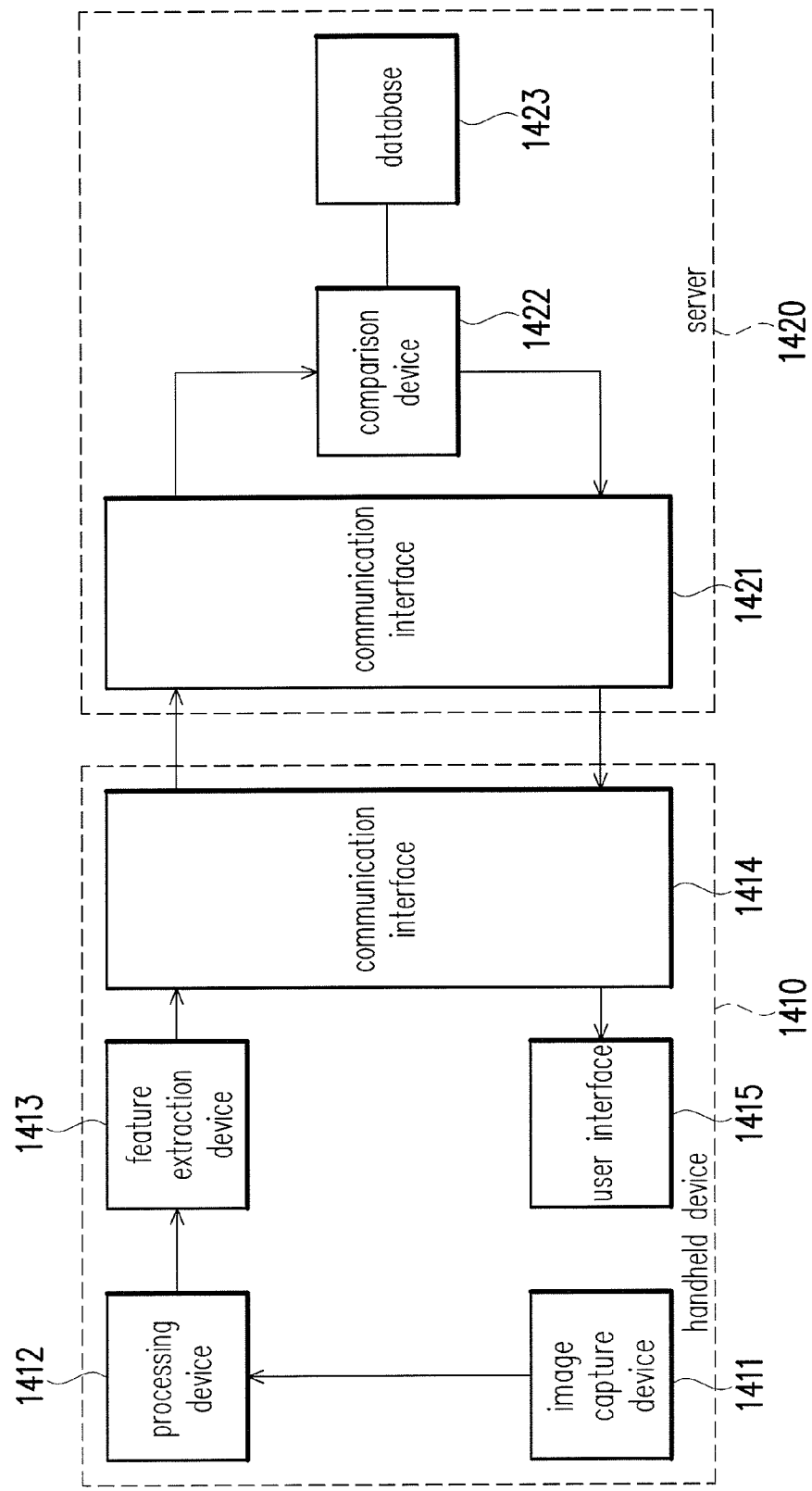
FIG. 14 is a functional block diagram of a system for diet management according to another embodiment of the present disclosure.

FIG. 14 is a functional block diagram of a system for diet management according to another embodiment of the present disclosure. The system for diet management in FIG. 14 includes a handheld device 1410 and a server 1420. The handheld device 1410 includes an image capture device 1411, a processing device 1412, a feature extraction device 1413, a communication interface 1414, and a user interface 1415. The handheld device 1410 may connect to a communication network such as an Internet or other networks via the communication interface 1414. The server 1420 includes a communication interface 1421, a comparison device 1422, and a database 1423. The server may connect to the communication network via the communication interface 1421. The image capture device 1411, the processing device 1412, the feature extraction device 1413, the comparison device 1422, the database, and the user interface 1415 may refer to the related description of the image capture device 410, the processing device 420, the feature extraction device 430, the comparison device 210, the database 220, and the user interface 440 in the embodiments in FIG. 14.

Referring to FIG. 13 and FIG. 14, the image capture device 1411 captures one or multiple diet images in Step S1311 (referring to the related description with more details in Step S111 in FIG. 3). The processing 1412 pre-processes the diet image in Step S1312 (referring to the related description with more details in Step S112 in FIG. 3). In Step S1312, the processing device 1412 may segment the original diet image into one or a plurality of diet regions for follow-up analysis processes specific to each of the diet regions. In Step S1312, the processing device 1412 may also segment one or a plurality of detailed food segment from the diet region. The feature extraction device 1413 extracts at least one diet image feature from each of the detailed food segments provided by the processing device 1412 in Step S1313. The feature extraction device 1413 generates a supervector based on the at least one diet image feature in Step S1314 (referring to the related description with more details in Step S114 in FIG. 3).

The handheld device 1410 and the server 1420 may communicate to each other via the communication interface 1414 and the communication interface 1421. Therefore, the feature extraction device 1413 may transfer the supervector to the server 1420 via the communication interface 1414.

The communication interface 1421 of the server 1420 may transfer the supervector provided by the handheld device 1410 to the comparison device 1422. The comparison device 1422 of the server 1420 performs similarity comparison between the supervector provided by the feature extraction device 1413 of the handheld device 1410 and other people's supervectors in the database 1423 so as to select at least one similar population in Step S1320 (referring to the related description with more details in Step S120 in FIG. 3).

In Step S1331, by using the multidimensional data of the similar population found in Step S1320, the comparison device 1422 may calculate at least one statistic of the similar population (referring to the related description with more details in Step S131 in FIG. 3). The server 1420 may transfer the statistic of the similar population to the handheld device 1410 via the communication interface 1421. The communication interface 1414 of the handheld device 1410 may transfer the statistic of the similar population provided by the server 1420 to the user interface 1415. In Step S1332, according to the statistic of the similar population found in Step S1331, the user interface 1415 provides the information related to the similar population to the user.

In other embodiments, the comparison device 1422 of the server 1420 may further use multidimensional data of at least one non-similar population for calculating at least one statistic of the non-similar population and comparing the statistics between the similar population and the non-similar population so as to provide a comparison result to the handheld device 1410 in Step S1331.

Figure 15:
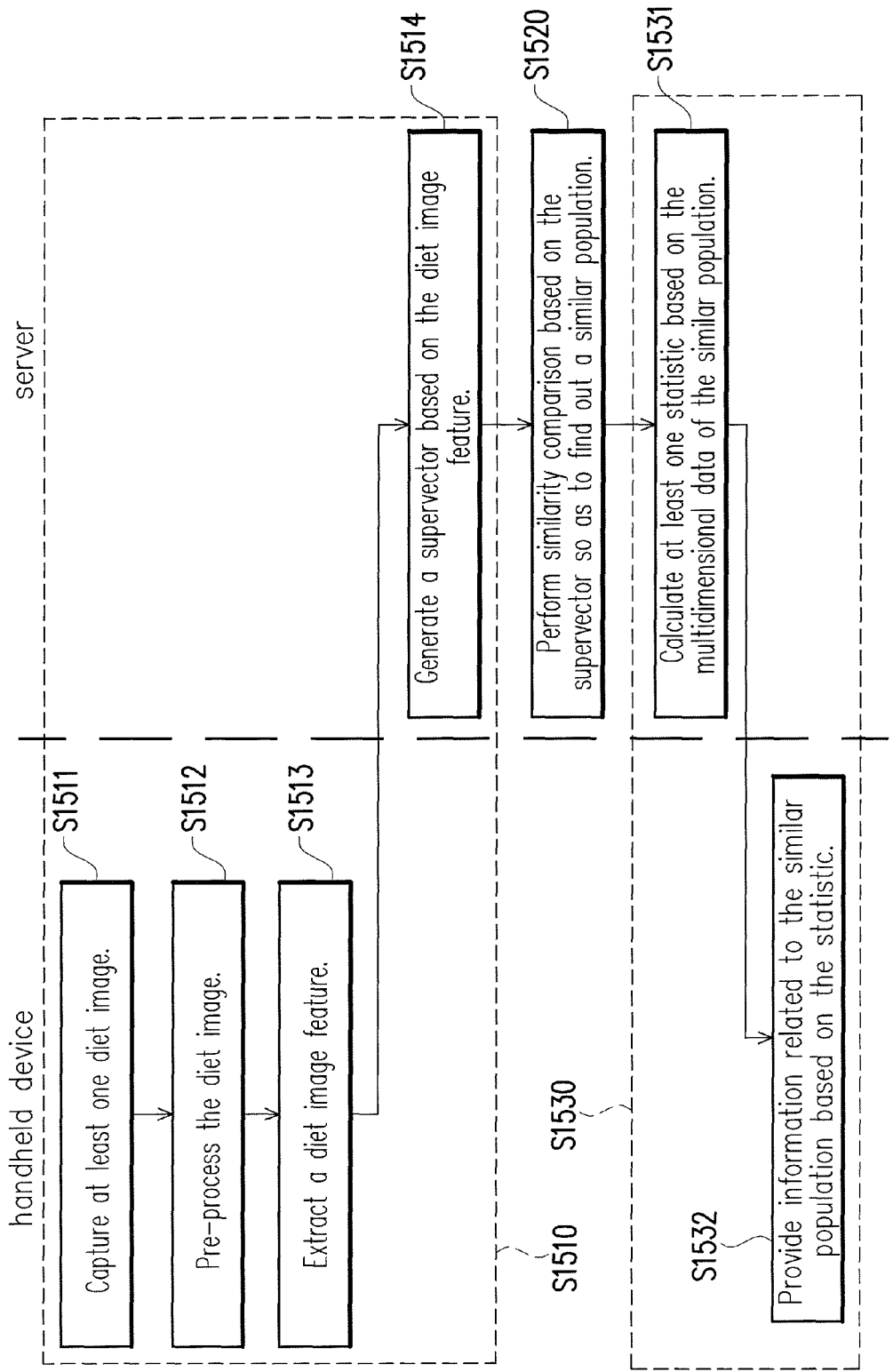
FIG. 15 is a flowchart of a method for diet management according to another embodiment of the present disclosure.

FIG. 15 is a flowchart of a computer-implemented method for diet management according to an embodiment of the present disclosure. Steps S1510-S1530 of the embodiment in FIG. 15 may refer to the related description in Steps S110-S130 in FIG. 1 and FIG. 3. The only difference from the embodiment in FIG. 3 is that Steps S1511, S1512, S1513, and S1532 in the embodiment in FIG. 15 are executed by a handheld device while Steps S1514, S1520, and S1531 are executed by a server.

Figure 16:
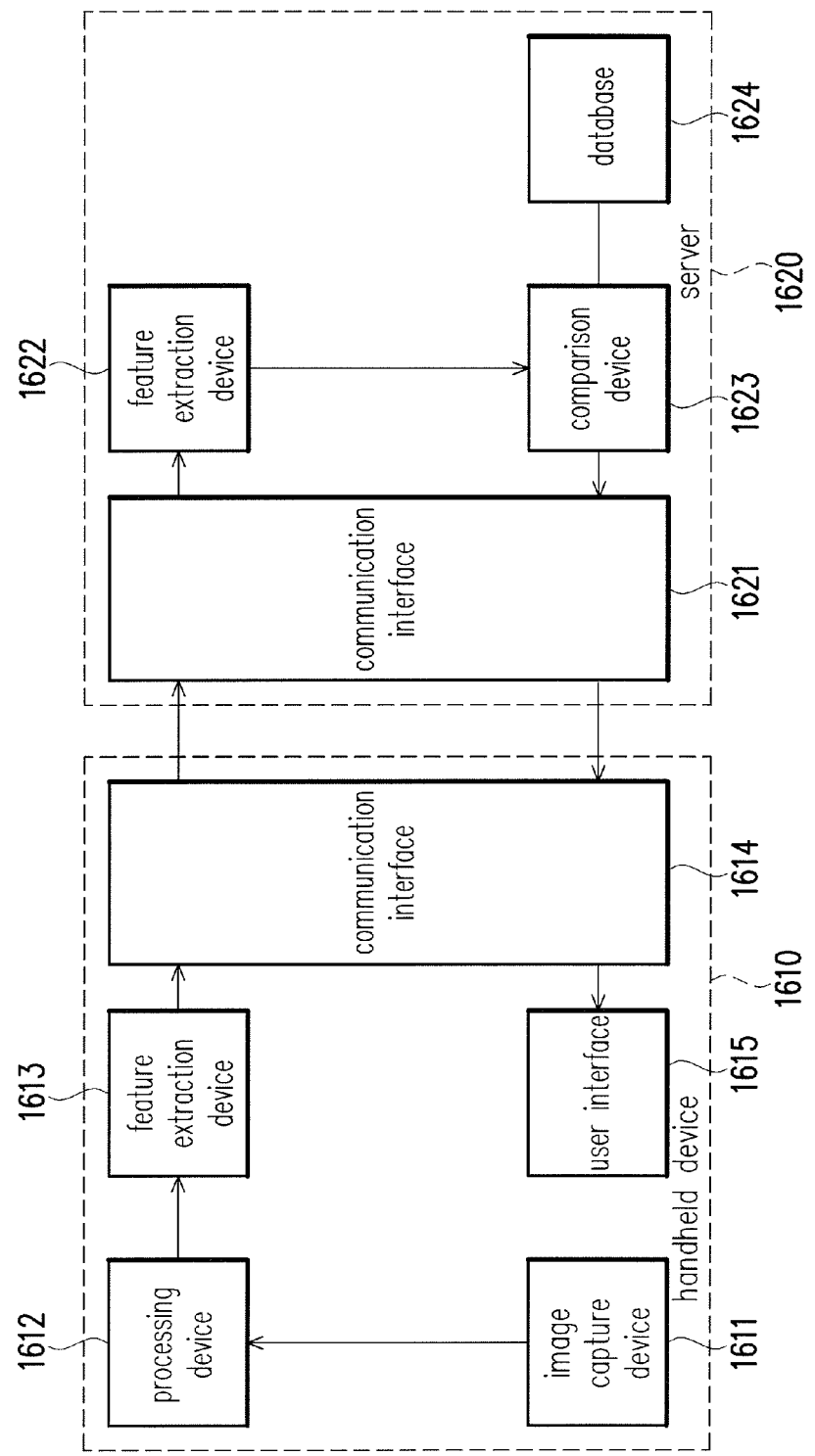
FIG. 16 is a functional block diagram of a system for diet management according to another embodiment of the present disclosure.

FIG. 16 is a function block diagram of a system for diet management according to an embodiment of the present disclosure. The system for diet management in FIG. 16 includes a handheld device 1610 and a server 1620. The handheld device 1610 includes an image capture device 1611, a processing device 1612, a feature extraction device 1613, a communication interface 1614, and a user interface 1615. The server 1620 includes a communication interface 1621, a feature extraction device 1622, a comparison device 1623, and a database 1624. The image capture device 1611, the processing device 1612, the feature capturing device 1613, the comparison device 1623, the database 1624, and the user interface in the embodiment in FIG. 16 may refer to the related description of the image capture device 410, the processing device 420, the feature extraction device 430, the comparison device 210, the database 220, and the user interface 440 in the embodiments of FIG. 2 and FIG. 4. The image capture device 1611, processing device 1612, the feature extraction device 1613, the communication interface 1614, the user interface 1615, the communication interface 1621, the comparison device 1623, and the database 1624 in the embodiment of FIG. 16 may refer to the related description of the image capture device 1411, the processing device 1412, the feature extraction device 1413, the communication interface 1414, the user interface 1415, the communication interface 1421, the comparison device 1422, and the database 1423 in the embodiment of FIG. 14. The only difference from the embodiment in FIG. 14 is that the server 1620 in the embodiment of FIG. 16 further includes the feature extraction device 1622.

Referring to FIG. 15 and FIG. 16, the image capture device 1611 captures one or multiple diet images in Step S1511 (referring to the related description with more details in Step S111 in FIG. 3). The processing device 1612 pre-processes the diet image in Step S1512 (referring to the related description with more details in Step S112 in FIG. 3). In Step S1512, the processing device 1612 may segment the original diet image into one or a plurality of diet regions for follow-up analysis processes specific to each of the diet regions. In Step S1512, the processing device 1612 may also segment one or a plurality of detailed food segments from the diet region. The feature extraction device 1613 extracts at least one diet image feature from each of the detailed food segments provided by the processing device 1612 in Step S1513 (referring to the related description with more details in Step S113 in FIG. 3).

The handheld device 1610 and the server 1620 may communicate to each other via the communication interface 1614 and the communication interface 1621. Therefore, the feature extraction device 1613 may transfer the diet image feature to the server 1620 via the communication interface 1614. The communication interface 1621 of the server 1620 may transfer the diet image feature provided by the handheld device 1610 to the feature extraction device 1622. The feature extraction device 1622 of the server 1620 generates a supervector based on the at least one diet image feature in Step S1514 (referring to the related description with more details in Step S114 in FIG. 3).

For example, the user may operate the handheld device 1610 during a lunch so as to capture a diet image of the lunch. By operating the handheld device 1610, a diet image feature may be extracted from the diet image of the lunch, and the diet image feature of the lunch may be transferred to the feature extraction device 1622 of the server 1620. During dinner, the user may capture a diet image of the dinner by using the handheld device 1610. By operating the handheld device 1610, a diet image feature may be extracted from the diet image of the dinner, and the diet image feature of the dinner may be transferred to the feature extraction device 1622 of the server 1620. The feature extraction device 1622 of the server 1620 may combine the diet image feature of the lunch and the diet image feature of the dinner to form a supervector.

The comparison device 1623 of the server 1620 performs similarity comparison between the supervector provided by the feature extraction device 1622 and other people's supervectors in the database 1624 so as to select at least one similar population in Step S1520 (referring to the related description with more details in Step S120 in FIG. 3).

In Step S1531, by using the multidimensional data of the similar population found in Step S1520, the comparison device 1623 may calculate at least one statistic of the similar population (referring to the related description with more details in Step S131 in FIG. 3). The server 1620 may transfer the statistic of the similar population to the handheld device 1610 via the communication interface 1621. The communication interface 1614 of the handheld device 1610 may transfer the statistic of the similar population provided by the server 1620 to the user interface 1615. In Step S1532, according to the statistic of the similar population found in Step S1531, the user interface 1615 provides the information related to the similar population to the user.

In other embodiments, the comparison device 1623 of the server 1620 may further use multidimensional data of at least one non-similar population for calculating at least one statistic of the non-similar population and comparing the statistics between the similar population and the non-similar population (referring to the related description with more details in Step S132 in FIG. 3, FIG. 11 and FIG. 12) so as to provide a comparison result to the handheld device 1610 in Step S1531.

Figure 17:
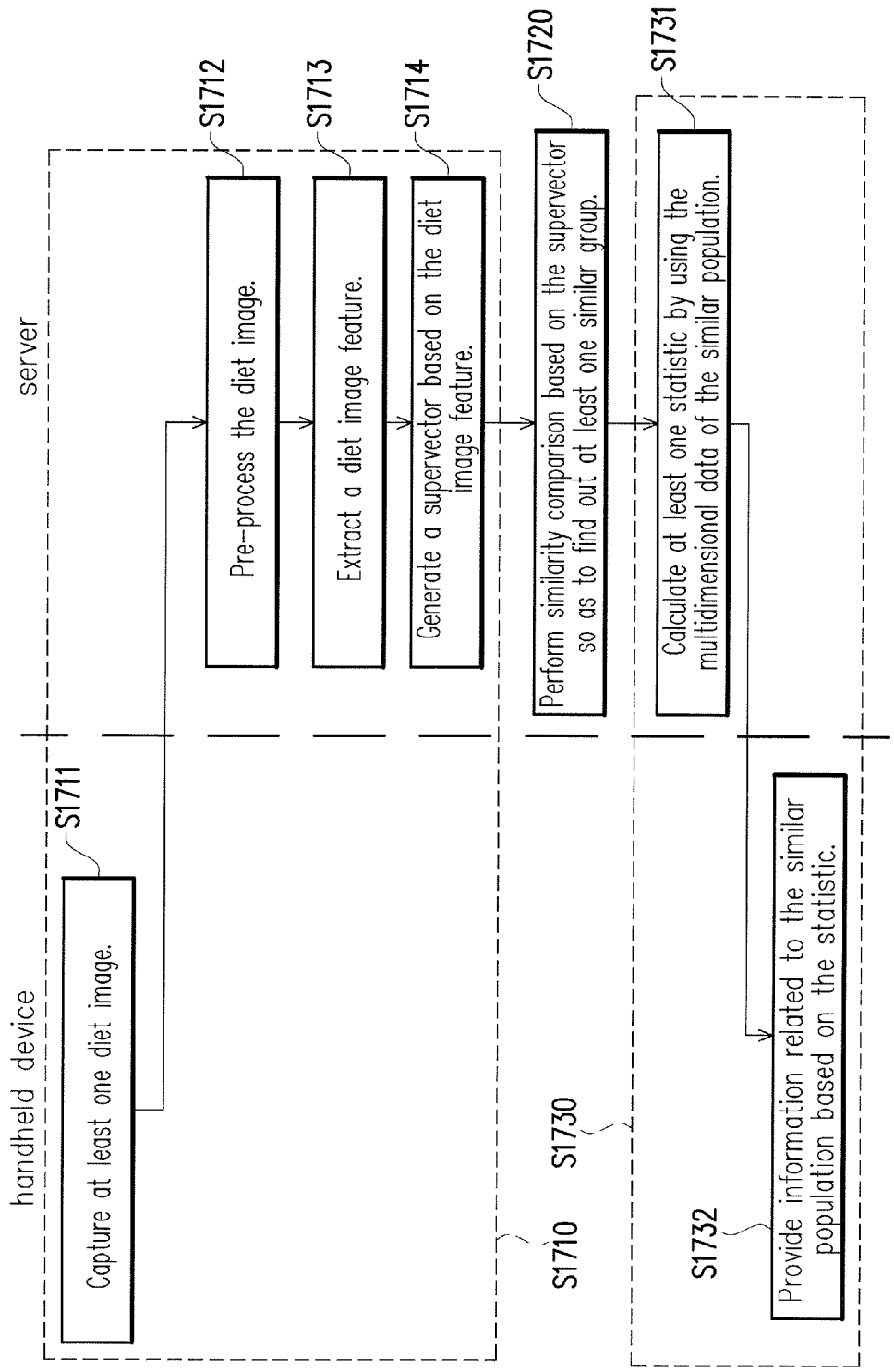
FIG. 17 is a flowchart of a method for diet management according to another embodiment of the present disclosure.

FIG. 17 is a flowchart of a computer-implemented method for diet management according to another embodiment of the present disclosure. Steps S1710-S1730 of the embodiments in FIG. 17 may refer to the related description of Steps S110-S130 in FIG. 1 and FIG. 3. The only difference from the embodiment in FIG. 3 is that Steps S1711 and S1732 of the embodiment in FIG. 17 are executed by a handheld device while Steps S1712, S1713, S1714, S1720, and S1731 are executed by a server.

Figure 18:
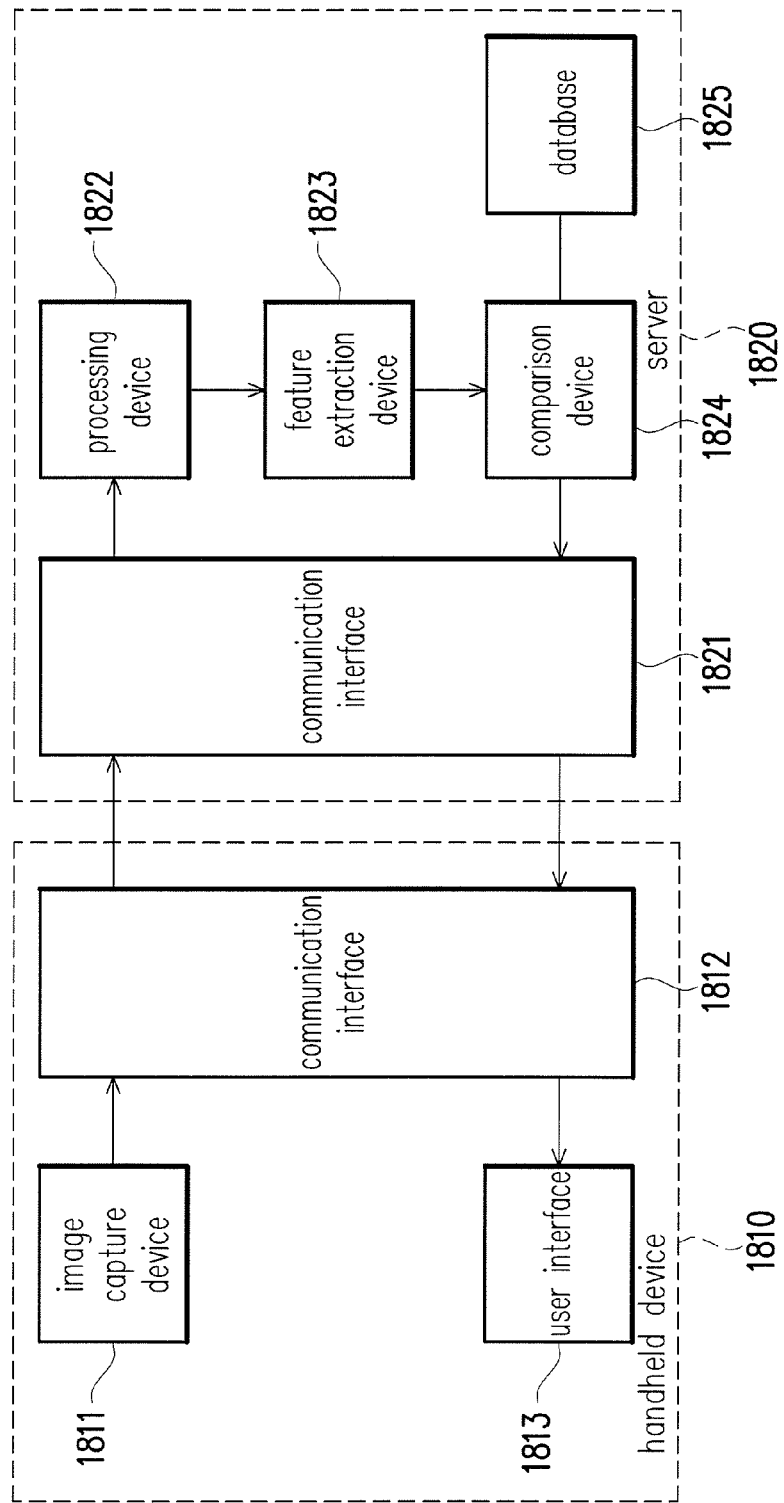
FIG. 18 is a functional block diagram of a system for diet management according to another embodiment of the present disclosure.

FIG. 18 is a functional block diagram of a system for diet management according to another embodiment of the present disclosure. The system for diet management in FIG. 18 includes a handheld device 1810 and a server 1820. The handheld device 1810 includes an image capture device 1811, a communication interface 1812, and a user interface 1813. The server 1820 includes a communication interface 1821, a processing device 1822, a feature extraction device 1823, a comparison device 1824, and a database 1825. The image capture device 1811, the processing device 1822, the feature extraction device 1823, the comparison device 1824, the database 1825, and the user interface 1813 of the embodiment in FIG. 18 may refer to the related description of the image capture device 410, the processing device 420, the feature extraction device 430, the comparison device 210, the database 220, and the user interface 440 of the embodiments in FIG. 2 and FIG. 4.

Referring to FIG. 17 and FIG. 18, the image capture device 1811 captures one or multiple diet images in Step S1711 (referring to the related description with more details in Step S111 in FIG. 3). The handheld device 1810 and the server 1820 may communicate to each other via the communication interface 1812 and the communication interface 1821. Therefore, the image capture device 1811 may transfer the diet image to the server 1820 via the communication interface 1812. The communication interface 1821 of the server 1820 may transfer the diet image provided by the handheld device 1810 to the processing device 1822.

The processing device 1822 of the server 1820 pre-processes the diet image in Step S1712 (referring to the related description with more details in Step S112 in FIG. 3). The processing device 1822 may segment the original diet image into one or a plurality of diet regions for follow-up analysis processes specific to each of the diet regions in Step S1712. In Step S1712, the processing device 1822 may also segment one or a plurality of detailed food segment from the diet region. The feature extraction device 1823 extracts at least one diet image feature from each of the detailed food segments provided by the processing device 1822 in Step S1713 (referring to the related description in more details in Step S113 in FIG. 3). The feature extraction device 1823 of the server 1820 generates a supervector based on the at least one diet image feature in Step S1714 (referring to the related description in more details in Step S114 in FIG. 3).

For example, the user may operate the handheld device 1810 during a lunch so as to capture a diet image of the lunch and upload the diet image of the lunch to the server 1820. The feature extraction device 1823 of the server 1820 may extract a diet image feature from the diet image of the lunch. During dinner, the user may capture a diet image of the dinner by using the handheld device 1810 and upload the diet image of the dinner to the server 1820. The feature extraction device 1823 of the server 1820 may extract a diet image feature from the diet image of the dinner. Therefore, the feature extraction device 1823 of the server 1820 may combine the diet image feature of the lunch and the diet image feature of the dinner to form a supervector.

The comparison device 1824 of the server 1820 performs similarity comparison between the supervector provided by the feature extraction device 1823 and other people's supervectors in the database 1825 so as to select at least one similar population in Step S1720 (referring to the related description in more details in Step S120 in FIG. 3). In Step S1731, by using the multidimensional data of the similar population found in Step S1720, the comparison device 1824 may calculate at least one statistic of the similar population (referring to the related description with more details in Step S131 in FIG. 3). The server 1820 may transfer the statistic of the similar population to the handheld device 1820 via the communication interface 1821. The communication interface 1812 of the handheld device 1810 may transfer the statistic of the similar population provided by the server 1820 to the user interface 1813. In Step S1732, according to the statistic of the similar population found in Step S1731, the user interface 1813 provides the information related to the similar population to the user.

In other embodiments, the comparison device 1824 of the server 1820 may further use the multidimensional data of at least one non-similar population for calculating at least one statistic of the non-similar group and comparing the statistics between the similar population and the non-similar population (referring to the related description with more details in Step S132 in FIG. 3, FIG. 11 and FIG. 12) so as to provide a comparison result to the handheld device 1810 in Step S1731.

Figure 19:
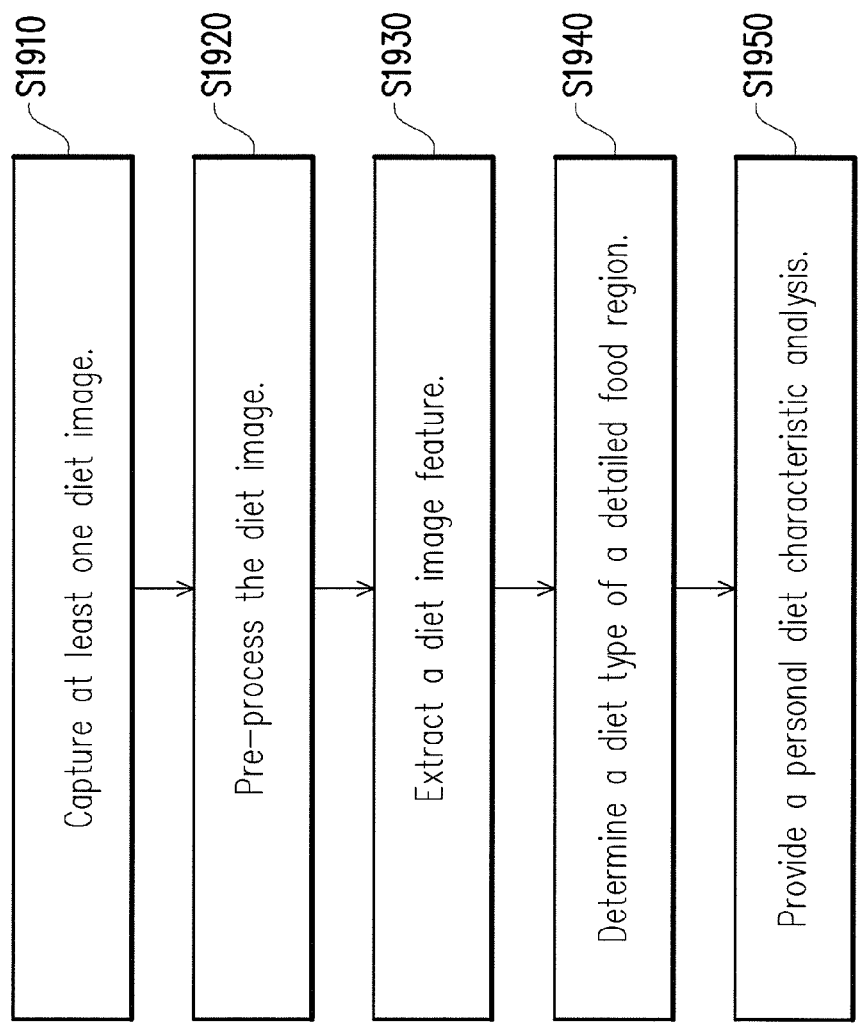
FIG. 19 is a flowchart of a method for diet management according to another embodiment of the present disclosure.

FIG. 19 is a flowchart of a system for diet management according to another embodiment of the present disclosure. The system for diet management such as a smart phone or other handheld devices captures at least one diet image via an image capture device (Step S1910). The system for diet management pre-processes the diet image so as to segment at least one diet region from the diet image and segment out at least one detailed food segment from the diet region (Step S1920). The system for diet management extracts at least one diet image feature from the detailed food segment (Step S1930). Steps S1910-S1930 of the embodiment in FIG. 19 may refer to the related description of Step S111-S113 in FIG. 3 and may be performed in a similar fashion.

The system for diet management performs similarity comparison in a database based on the diet image feature or determines the diet types of the detailed food segment via a diet type classifier (Step S1940). For example, a similarity comparison is performed between the food image feature and at least one feature vectors in the database so as to determine the diet types of the detailed food segment. The similarity comparison may refer to the calculation of an Euclidean distance, an angle, a correlation coefficient, or mutual information between the diet image feature and the feature vectors in the database. Step S1940 of the embodiment in FIG. 19 may refer to the related description of Step S120 in FIG. 1 and FIG. 3 and may be performed in a similar fashion.

The determination of the detailed food segment in diet characteristics may include the determination on the types and amount of the six categories of the food from Diet Pyramid (grains, vegetables, fruits, oils, meat and beans, and milk), the five categories of the food from Health Plate (grains, vegetables, fruits, protein, and milks), and the food from the five elements and the five colors (wood/green, fire/red, earth/yellow, gold/white, and water/black).

The system for diet management provides a personal diet characteristic analysis to the user based on the diet type and the area of the detailed food segment (Step S1950). The goal of the personal diet characteristic analysis is to determine whether the diet of the user is healthy and balanced from the information of each of the detailed food segments of each diet image captured by the user based on the primary diet rules defined by Food Pyramid, Health Dish, or the food from five elements and five colors.

In some embodiments, according to each classification result in Step S1940, the system for diet management may analyze a personal diet characteristic statistically by accumulating one or multiple diet images. For example, whether a diet is harmonic may be determined from the perspective of the five elements and the five colors; whether a diet is balanced may be determined from the perspective of Health Dish.

To sum up, the method and the system for diet management disclosed in the aforementioned embodiments may assist the user to achieve self-health management based on the result of the analysis on balance characteristic and/or the comparison of the population information provided by the system. The method and the system for diet management disclosed in the embodiments in the aforementioned embodiments includes at least the followings:

1. By using a training model-based diet region segmentation method which defines the color of the common food, the distribution of the color of the collected training diet images may be a basis for diet region segmentation for improving the complicated computation of conventional algorithms.
2. A feature extraction in diet characteristic with a concept of magnitude measurement is included. A feature vector is set according to the statistical diagram of the length coding in the diet region. Besides the magnitude information, the statistical information of the variation of the orientation of the texture of the diet image substantially includes a physical meaning. The flow of the feature extraction in the aforementioned embodiment may extract the concluded characteristic of the diet image.
3. Based on the method adapted in the aforementioned embodiments, the integrated region matching and the image region matching are combined and a similarity between two diet images is calculated. Furthermore, the concept is extended to a diet image series by comparing a daily diet image series of the user with those of other users and return information of a population with a similar diet habit so as to assist the user to understand an outcome of such diet habit for self-health management.

It will be apparent to those skilled in the art that various modifications and variations can be made to the structure of the disclosed embodiments without departing from the scope or spirit of the disclosure. In view of the foregoing, it is intended that the disclosure cover modifications and variations of this disclosure provided they fall within the scope of the following claims and their equivalents.

What is claimed is:

1. A computer-implemented method for diet management, adapted to a diet management system comprising a computer and a memory device used as a database, the computer comprises a processor and a plurality of program instructions, wherein the plurality of program instructions are loaded into the processor to perform the computer-implemented method, and the computer-implemented method comprising:
    capturing at least one diet image via an image capture device;
    pre-processing the at least one diet image so as to obtain at least one diet region from the at least one diet image and obtain at least one detailed food segment from the diet region;
    extracting at least one diet image feature from the at least one detailed food segment;
    generating a supervector based on the at least one diet image feature;
    performing similarity comparison between the supervector and at least one feature vectors in the database to determine a diet type of the at least one detailed food segment and to determine at least one similar population;
    providing information related to the similar population; and
    providing a personal diet characteristic analysis based on the diet type and an area of the at least one detailed food segment,
    wherein the providing the information related to the similar population comprises:
        calculating at least one statistic of the similar population by using at least one multidimensional data of the similar population; and
        providing the information related to the similar population based on the statistic of the similar population.

2. The method for diet management of claim 1, wherein the pre-processing the at least one diet image comprises:
    transforming the at least one diet image to a normalized space.

3. The method for diet management of claim 1, wherein the pre-processing the at least one diet image comprises:
    performing color correction, bright correction, or white balance correction on the at least one diet image;
    performing background removal on the at least one diet image so as to obtain the at least one diet region; and
    performing detailed food segment segmentation on the at least one diet region so as to segment out the at least one detailed food segment from the diet region.

4. The method for diet management of claim 1, wherein the at least one image feature comprises image capturing time, image capturing location, color, texture complexity, or reflectivity.

5. The method for diet management of claim 1, wherein the performing similarity comparison comprises:
    calculating an Euclidean distance, an angle, a correlation coefficient, or mutual information between the supervector and one of the feature vectors in the database.

6. The method for diet management of claim 1, wherein the determining the diet type of the at least one detailed food segment comprises:
    performing the similarity comparison in the database or via a diet type classifier.

7. A system for diet management comprising a computer and a memory device used as a database, the computer comprises a processor and a plurality of program instructions, wherein the plurality of program instructions are loaded into the processor to perform the following operations:
    capturing at least one diet image via an image capture device;

pre-processing the at least one diet image so as to obtain at least one diet region from the at least one diet image and obtain at least one detailed food segment from the diet region;

extracting at least one diet image feature from the at least one detailed food segment;

generating a supervector based on the at least one diet image feature;

performing similarity comparison between the supervector and at least one feature vectors in the database to determine a diet type of the at least one detailed food segment and to determine at least one similar population;

providing information related to the similar population; and providing a personal diet characteristic analysis based on the diet type and an area of the at least one detailed food segment, wherein the providing the information related to the similar population comprises:

calculating at least one statistic of the similar population by using at least one multidimensional data of the similar population; and providing the information related to the similar population based on the statistic of the similar population.

8. The system for diet management of claim 7, wherein the operation of pre-processing the at least one diet image comprises:

transforming the at least one diet image to a normalized space.

9. The system for diet management of claim 7, wherein the operation of pre-processing the at least one diet image comprises:

performing color correction, bright correction, or white balance correction on the at least one diet image;

performing background removal on the at least one diet image so as to obtain the at least one diet region; and performing detailed food segment segmentation on the at least one diet region so as to segment out the at least one detailed food segment from the diet region.

10. The system for diet management of claim 7, wherein the at least one image feature comprises image capturing time, image capturing location, color, texture complexity, or reflectivity.

11. The system for diet management of claim 7, wherein the performing similarity comparison comprises:

calculating an Euclidean distance, an angle, a correlation coefficient, or mutual information between the supervector and one of the feature vectors in the database.

12. The system for diet management of claim 7, wherein the operation of determining the diet type of the at least one detailed food segment comprises:

performing the similarity comparison in the database or via a diet type classifier.

13. An electronic device comprising:

a database; and a processing circuit, electrically coupled to the database, for capturing at least one diet image via an image capture device, pre-processing the at least one diet image so as to obtain at least one diet region from the at least one diet image and obtain at least one detailed food segment from the diet region, extracting at least one diet image feature from the at least one detailed food segment, generating a supervector based on the at least one diet image feature, performing similarity comparison between the supervector and at least one feature vectors in the database to determine a diet type of the at least one detailed food segment, providing information related to the similar population, and providing a personal diet characteristic analysis based on the diet type and an area of the at least one detailed food segment, wherein processing circuit calculates at least one statistic of the similar population by using at least one multidimensional data of the similar population, and provides the information related to the similar population based on the statistic of the similar population.

14. The electronic device of claim 13, wherein the processing circuit transforms the at least one diet image to a normalized space.

15. The electronic device of claim 13, wherein the processing circuit performs color correction, bright correction, or white balance correction on the at least one diet image, the processing circuit performs background removal on the at least one diet image so as to obtain the at least one diet region, and the processing circuit performs detailed food segment segmentation on the at least one diet region so as to segment out the at least one detailed food segment from the diet region.

16. The electronic device of claim 13, wherein the at least one image feature comprises image capturing time, image capturing location, color, texture complexity, or reflectivity.

17. The electronic device of claim 13, wherein the processing circuit calculates an Euclidean distance, an angle, a correlation coefficient, or mutual information between the supervector and one of the feature vectors in the database.

18. The electronic device of claim 13, wherein the processing circuit performs the similarity comparison in the database or via a diet type classifier.

* * * * *